United States Patent
Truckai

(10) Patent No.: US 9,907,556 B2
(45) Date of Patent: Mar. 6, 2018

(54) POLYMER COMPOSITES FOR BIOMEDICAL APPLICATIONS AND METHODS OF MAKING

(71) Applicant: DFINE, INC., South Jordan, UT (US)

(72) Inventor: Csaba Truckai, Saratoga, CA (US)

(73) Assignee: DFine, Inc., South Jordan, UT (US)

( * ) Notice: Subject to any disclaimer, the term of this patent is extended or adjusted under 35 U.S.C. 154(b) by 223 days.

(21) Appl. No.: 14/309,248

(22) Filed: Jun. 19, 2014

(65) Prior Publication Data

US 2014/0371734 A1 Dec. 18, 2014

Related U.S. Application Data

(60) Continuation of application No. 12/797,453, filed on Jun. 9, 2010, now Pat. No. 8,771,265, which is a
(Continued)

(51) Int. Cl.
*A61B 18/12* (2006.01)
*A61B 17/12* (2006.01)
(Continued)

(52) U.S. Cl.
CPC .... *A61B 17/12113* (2013.01); *A61B 17/1214* (2013.01); *A61B 17/12022* (2013.01);
(Continued)

(58) Field of Classification Search
CPC ........ A61B 17/12022; A61B 17/12045; A61B 17/12113; A61B 17/12118; A61B 17/12136; A61B 17/1214; A61B 17/12168; A61B 17/12181; A61B 17/12186; A61B 18/04; A61B 2017/12068;
(Continued)

(56) References Cited

U.S. PATENT DOCUMENTS 3,359,145 A 12/1967 Salyer et al.
3,434,996 A 3/1969 Dollman et al.
(Continued)

FOREIGN PATENT DOCUMENTS

WO 2002087416 11/2002
WO 2006031490 3/2006

OTHER PUBLICATIONS

International Search Report and Written Opinion dated May 31, 2006 for PCT/US2005/044055.
(Continued)

*Primary Examiner* — Daniel Fowler
(74) *Attorney, Agent, or Firm* — Stoel Rives LLP

(57) ABSTRACT

A biomedical polymer composite that exhibits ultra-low thermal conductivity properties. In a preferred embodiment, the biomedical polymer composite comprises a base polymer component with a dispersed thermally non-conductive filler component consisting of glass or ceramic nanospheres or microspheres that have a thermal conductivity of less than 5 W/m-K, and preferably less than 2 W/m-K. In one embodiment, the polymer composite has an electrically conductive filler and can be used in a filament for treating arteriovascular malformations. In another embodiment, the polymeric composite can be used as an energy-coupling means to apply energy to tissue.

16 Claims, 34 Drawing Sheets

Related U.S. Application Data continuation of application No. 12/509,168, filed on Jul. 24, 2009, now abandoned, which is a division of application No. 10/790,987, filed on Mar. 2, 2004, now Pat. No. 7,569,626, which is a continuation-in-part of application No. 10/456,149, filed on Jun. 5, 2003, now Pat. No. 6,958,061.

(51) Int. Cl.
*D04H 1/42* (2012.01)
*A61B 18/04* (2006.01)
*A61B 18/00* (2006.01)

(52) U.S. Cl.
CPC .. *A61B 17/12045* (2013.01); *A61B 17/12118* (2013.01); *A61B 17/12136* (2013.01); *A61B 17/12168* (2013.01); *A61B 17/12181* (2013.01); *A61B 17/12186* (2013.01); *A61B 18/04* (2013.01); *D04H 1/42* (2013.01); *A61B 2017/12068* (2013.01); *A61B 2017/12072* (2013.01); *A61B 2018/00416* (2013.01); *A61B 2018/00589* (2013.01); *Y10T 428/249924* (2015.04)

(58) Field of Classification Search
CPC A61B 2017/12072; A61B 2018/00416; A61B 2018/00589
See application file for complete search history.

(56) References Cited

U.S. PATENT DOCUMENTS

| | | |
|---|---|---|
| 3,828,780 A | 8/1974 | Morrison, Jr. |
| 3,833,546 A | 9/1974 | Takekoshi et al. |
| 3,847,888 A | 11/1974 | Baumgaertner |
| 4,294,251 A | 10/1981 | Grennwald et al. |
| 4,338,925 A | 7/1982 | Miller |
| 4,653,501 A | 3/1987 | Cartmell et al. |
| 4,790,311 A | 12/1988 | Ruiz |
| 4,943,290 A * | 7/1990 | Rexroth ............ A61B 18/1485 606/45 |
| 4,969,888 A | 11/1990 | Scholten et al. |
| 4,983,648 A | 1/1991 | Laughner et al. |
| 5,078,736 A | 1/1992 | Behl |
| 5,098,429 A | 3/1992 | Sterzer |
| 5,108,404 A | 4/1992 | Scholten et al. |
| 5,108,407 A | 4/1992 | Geremia |
| 5,122,136 A | 6/1992 | Guglielmi |
| 5,151,100 A | 9/1992 | Abele et al. |
| 5,178,618 A | 1/1993 | Kandarpa |
| 5,226,430 A | 7/1993 | Spears et al. |
| 5,226,889 A | 7/1993 | Sheiban |
| 5,330,527 A | 7/1994 | Montecalvo et al. |
| 5,331,959 A | 7/1994 | Imran |
| 5,354,295 A | 10/1994 | Guglielmi |
| 5,431,654 A | 7/1995 | Nic |
| 5,500,287 A | 3/1996 | Henderson |
| 5,507,744 A | 4/1996 | Tay et al. |
| 5,514,135 A | 5/1996 | Earle |
| 5,522,836 A | 6/1996 | Palermo |
| 5,562,720 A | 10/1996 | Stern et al. |
| 5,582,609 A | 12/1996 | Swanson et al. |
| 5,685,847 A | 11/1997 | Barry |
| 5,693,099 A | 12/1997 | Harle |
| 5,713,974 A | 2/1998 | Martin et al. |
| 5,749,894 A | 5/1998 | Engelson |
| 5,759,182 A | 6/1998 | Varney et al. |
| 5,797,903 A | 8/1998 | Swanson et al. |
| 5,811,314 A | 9/1998 | Chen et al. |
| 5,814,039 A | 9/1998 | Prescott |
| 5,851,206 A | 12/1998 | Guglielmi |
| 5,976,131 A | 11/1999 | Guglielmi |
| 6,024,754 A | 2/2000 | Engelson |
| 6,033,401 A | 3/2000 | Edwards et al. |
| 6,035,238 A * | 3/2000 | Ingle ............... A61B 18/1485 607/101 |
| 6,053,910 A | 4/2000 | Fleenor |
| 6,066,132 A | 5/2000 | Chen et al. |
| 6,171,312 B1 | 1/2001 | Beaty |
| 6,179,862 B1 | 1/2001 | Sawhney |
| 6,193,708 B1 | 2/2001 | Ken et al. |
| 6,207,077 B1 | 3/2001 | Burnell-Jones |
| 6,216,704 B1 | 4/2001 | Ingle et al. |
| 6,228,904 B1 | 5/2001 | Yadav et al. |
| 6,231,573 B1 | 5/2001 | Amor et al. |
| 6,231,615 B1 | 5/2001 | Preissman |
| 6,235,043 B1 | 5/2001 | Reiley et al. |
| 6,235,801 B1 | 5/2001 | Morales et al. |
| 6,241,914 B1 | 6/2001 | Schleifstein |
| 6,280,456 B1 | 8/2001 | Scribner et al. |
| 6,284,809 B1 | 9/2001 | Plummer et al. |
| 6,309,420 B1 | 10/2001 | Preissman |
| 6,317,615 B1 | 11/2001 | Kenknight et al. |
| 6,383,181 B1 | 5/2002 | Johnson et al. |
| 6,439,439 B1 | 8/2002 | Rickard et al. |
| 6,458,127 B1 | 10/2002 | Truckai et al. |
| 6,464,716 B1 | 10/2002 | Dobak et al. |
| 6,493,589 B1 | 12/2002 | Medkhour et al. |
| 6,511,477 B2 | 1/2003 | Altman et al. |
| 6,640,137 B2 | 10/2003 | MacDonald |
| 6,652,058 B2 | 11/2003 | Kanematsu et al. |
| 6,652,968 B1 | 11/2003 | Miller et al. |
| 6,786,904 B2 | 9/2004 | Doscher et al. |
| 6,814,736 B2 | 11/2004 | Reiley et al. |
| 6,958,061 B2 | 10/2005 | Truckai et al. |
| 6,979,352 B2 | 12/2005 | Reynolds |
| 7,115,163 B2 | 10/2006 | Zimmerman |
| 7,160,020 B2 | 1/2007 | Sand |
| 7,306,598 B2 | 12/2007 | Truckai et al. |
| 2002/0026195 A1 | 2/2002 | Layne et al. |
| 2002/0082608 A1 | 6/2002 | Reiley et al. |
| 2002/0090501 A1 | 7/2002 | Tobita |
| 2002/0128336 A1 | 9/2002 | Kolb et al. |
| 2002/0147497 A1 | 10/2002 | Belef et al. |
| 2002/0156483 A1 | 10/2002 | Voellmicke et al. |
| 2003/0220648 A1 | 1/2003 | Osorio et al. |
| 2003/0032929 A1 | 2/2003 | McGuckin |
| 2003/0130738 A1 | 7/2003 | Hovda et al. |
| 2003/0216724 A1 | 11/2003 | Jahns |
| 2003/0233096 A1 | 12/2003 | Osorio et al. |
| 2004/0006347 A1 | 1/2004 | Sproul |
| 2004/0024410 A1 | 2/2004 | Olson et al. |
| 2004/0044341 A1 | 3/2004 | Truckai et al. |
| 2004/0092948 A1 | 5/2004 | Stevens et al. |
| 2004/0102845 A1 | 5/2004 | Reynolds |
| 2004/0087936 A1 | 6/2004 | Stern et al. |
| 2004/0193171 A1 | 9/2004 | DiMauro et al. |
| 2004/0102573 A1 | 11/2004 | Sagal et al. |
| 2004/0225296 A1 | 11/2004 | Reiss et al. |
| 2004/0228898 A1 | 11/2004 | Ross et al. |
| 2004/0267271 A9 | 12/2004 | Scribner et al. |
| 2004/0267272 A1 | 12/2004 | Henniges et al. |
| 2005/0010231 A1 | 1/2005 | Myers |
| 2005/0059979 A1 | 3/2005 | Yetkinler et al. |
| 2005/0222681 A1 | 10/2005 | Richley et al. |
| 2005/0245938 A1 | 11/2005 | Kochan |
| 2005/0267467 A1 | 12/2005 | Paul |
| 2006/0052743 A1 | 3/2006 | Reynolds |
| 2006/0074433 A1 | 4/2006 | McGill et al. |
| 2006/0079905 A1 | 4/2006 | Beyar et al. |
| 2006/0095138 A1 | 5/2006 | Truckai et al. |
| 2006/0122621 A1 | 6/2006 | Truckai et al. |
| 2006/0122622 A1 | 6/2006 | Truckai et al. |
| 2006/0122623 A1 | 6/2006 | Truckai et al. |
| 2006/0122624 A1 | 6/2006 | Truckai et al. |

(56) References Cited

U.S. PATENT DOCUMENTS

2006/0122625 A1    6/2006   Truckai et al.
2007/0022912 A1    2/2007   Zimmermann

OTHER PUBLICATIONS

International Search Report and Written Opinion dated Jun. 20, 2006 for PCT/US2005/043984.
Notice of Allowance dated Jul. 30, 2007 for U.S. Appl. No. 10/456,113.
Office Action dated Mar. 6, 2007 for U.S. Appl. No. 10/456,113.
Office Action dated Jul. 25, 2005 for U.S. Appl. No. 10/456,113.
Carrodeguas, et al., Injectable Acrylic Bone Cements for Vertebroplasty with Improved Properties, Journal of Biomedical Materials Research, XP002312783, vol. 68 No. 1 ,Jan. 15, 2004 ,94-104.

* cited by examiner

POLYMER COMPOSITES FOR BIOMEDICAL APPLICATIONS AND METHODS OF MAKING

CROSS-REFERENCE TO RELATED APPLICATIONS

This application is a continuation of U.S. patent application Ser. No. 12/797,453, filed Jun. 9, 2010, which is a continuation of U.S. patent application Ser. No. 12/509,168, filed Jul. 24, 2009, now abandoned, which is a divisional of U.S. patent application Ser. No. 10/790,987, filed Mar. 2, 2004, now U.S. Pat. No. 7,569,626, which is a continuation-in-part of U.S. patent application Ser. No. 10/456,149 filed Jun. 5, 2003, now U.S. Pat. No. 6,958,061, the disclosures of which are incorporated herein by reference in their entirety. This application is also related to U.S. patent application Ser. No. 10/779,075 filed Feb. 14, 2004 which is incorporated herein by reference.

FIELD OF THE INVENTION

This invention relates to a biomedical polymer composite that exhibits ultra-low thermal conductivity properties as well as optional electrical resistivity. In one embodiment, the polymer composite is formed into an embolic filament for occluding an arteriovascular malformation (AVM) wherein electrical energy can be used to sacrifice, melt and divide any suitable length of the filament for filling the AVM without any collateral thermal effects within the vessel lumen.

BACKGROUND OF THE INVENTION

Various devices and techniques have been developed for occluding aneurysms or other vascular deformations. A common type of aneurysm treatment utilizes a detachable coil that is fed into the aneurysm to substantially occupy the aneurysm volume. The typical approach for implanting an embolic coil in an aneurysm involves attaching the coil to the distal end of a pushwire, and introducing the pushwire and coil through a catheter lumen until the coil is pushed into the aneurysm. The typical manner of detaching the coil from the pushwire involves using a direct current to cause electrolysis of a sacrificial joint between the pushwire and the coil. The coil can then serve to mechanically occlude a significant volume of the aneurysm and thereby reduce blood circulation within the aneurysm. After a period of time ranging from several hours to several weeks, the volume of the aneurysm can become fully occluded as blood clots about the coil. Eventually, the aneurysm will be reduced and reabsorbed by the body's natural wound healing process. This type of vaso-occlusion system was disclosed by Guglielmi in U.S. Pat. Nos. 5,122,136 and 5,354,295.

Another manner of treating an aneurysm was disclosed by Guglielmi (see U.S. Pat. Nos. 5,976,131; 5,851,206) and is described as electrothrombosis. In this particular approach, a catheter and pushwire are used to push a wire coil into the aneurysm that is connected to an electrical source. The system then delivers radiofrequency (Rf) current to the coil which is adapted to heat the blood volume within the aneurysm to cause thermal formation of thrombus (see U.S. Pat. No. 5,851,206; Col. 5, line 5). The conductive coil disclosed by Guglielmi in U.S. Pat. No. 5,976,131 has an insulated tip or other arrangements of insulation around the coil to prevent localized "hot spots" (see U.S. Pat. No. 5,976,131; Col. 3, line 53).

It is believed that several risk factors are involved in any uncontrolled use of significant levels of Rf energy to cause so-called electrothrombosis. Most important, the use of electrical energy to cause current flow between a coil (first electrode) within an aneurysm and a ground (a second body electrode) will likely cause high energy densities and highly localized heating of tissue that comes into contact with the coil. If the wall of the aneurysm contacts the energized portion of a coil, there is a significant danger of perforation or ablation of the aneurysm wall that could be life-threatening. Further, the use of uncontrolled energy delivery to an implanted coil could heat adjacent brain tissue to excessive levels resulting in loss of brain function or even death. For these reasons, the coils disclosed by Guglielmi were provided with an insulating material covering the tip of the coil that is most likely to come into contact the wall of the aneurysm. However, it is still likely that unwanted localized heating will occur within the aneurysm sac when attempting to cause ohmic heating of the blood volume in an aneurysm by creating Rf current flow between an electrode coil and a body electrode.

Another disadvantage of using the typical commercially available wire coil is that the physician must estimate dimensions and volume of the aneurysm and then feed multiple coils into the aneurysm. The deployment of each coil is time consuming, and the detachment of the coil from the introducer pushwire also is time consuming.

SUMMARY OF THE INVENTION

In general, this invention comprises a vascular occlusion system for treating aneurysms that provides a novel class of polymer composite embolic elements that carry thin conductive coatings or conductive fillers to provide the composite with a specified resistivity to electrical current flow. The embolic element is introduced into a targeted site in a patient's vasculature by a microcatheter sleeve. The thin metallic coating allows the embolic element to be soft and flexible, and more importantly, allows the physician to select any desired length (and volume) of embolic element in vivo for causing mechanical occlusion of the aneurysm. The system of the invention also provides an electrical source and computer controller for feedback modulation of power delivery with a first (low) range and a second (high) range to accomplish two different methods of the invention. The electrical source is coupled to an electrode arrangement at the distal terminus of the catheter sleeve that contacts the surface of the embolic element as it is slidably deployed from the catheter. Thus, energy is delivered to resistive embolic element directly from the distal terminus of the catheter sleeve. The catheter working end also carries a thermocouple, coupled to feedback circuitry, for sensing the temperature of the deployed embolic element and controlling its temperature via power modulation.

In a method of using an exemplary system, the physician pushes the embolic element from the distal terminus of a catheter into a targeted site in a patient's vasculature to thereby mechanically occlude the aneurysm or other vascular malformation. After disposing a selected length of the embolic element within the targeted site, the physician can optionally actuate the electrical source to deliver low power electrical current from the electrode(s) at the catheter's distal terminus. The electrical energy delivery to the embolic element causes slight resistive heating of the element's surface to formation of layer of coagulum about the deployed embolic element. By this means, the system can controllably create a selected thickness of coagulum about the surface of the embolic element. Thus, the initial deployment of the selected length of the embolic element mechanically occludes or occupies a selected (first) volume of a vascular malformation. Thereafter, controlled energy delivery thermally induces a layer of coagulative to form, thereby providing another selected volume of material to occlude the vascular malformation.

In the next manner of practicing a method of the invention, the physician directs the controller and electrical source to deliver current at a second (higher) power level to the embolic element from the same electrode arrangement at the catheter's distal end. This second power level causes the polymeric element to act like a fuse and divide at the catheter sleeve's terminus. This selected power level, within a fraction of a second, can thermally melt or divide the deployed portion of the continuous polymer embolic element from the remainder of the element still within the catheter sleeve. This aspect of the method of the invention allows the physician to select any length of embolic element intra-operatively under fluoroscopy, which is not possible in the prior art.

In another embodiment of the invention, the polymer composite is adapted for embolic filaments as well other thermally-related medical therapies, wherein the composite comprise a base polymer component with a dispersed thermally non-conductive filler component. In preferred embodiments, the insulative filler comprises glass or ceramic nanospheres or microspheres. The filler component has a thermal conductivity of less than 5 W/m-K, and preferably less than 2 W/m-K.

In an vaso-occlusive application, the conductively-doped polymer composite with insulative glass microspheres therein can act like a fuse and the insulative properties can further prevent transfer of thermal effects to adjacent body media.

In another embodiment, the conductively-doped polymer composite with an insulative filler can be used in sacrificial shells of a sphere or tubule that carries a releasable agent. For embolic filaments and sacrificial microspheres, the improvement is that the polymeric composition can have much higher sensitivity to applied electrical energy to sacrifice much more quickly while at the same time preventing any thermal spread away from the targeted polymer.

In other embodiments, the polymer composite with insulative glass microspheres therein can perform as a insulator gel to apply to tissue to protect against thermal damage from an unrelated treatment.

In a vaso-occlusive application, the invention advantageously provides a system and method for intra-operatively disposing any selected length and selected volume of an embolic element in a targeted site in a patient's vasculature to mechanically occlude a malformation.

The invention provides an embolic member with a specified resistivity by fabricating the a polymer member with at least one very thin conductive surface layer.

The invention provides an embolic member with a specified resistivity by fabricating the polymer extrusion with conductive microfilaments embedded therein.

The invention provides an embolic member with a specified resistivity by extruding a polymer matrix with conductive particles embedded therein.

BRIEF DESCRIPTION OF THE DRAWINGS

Other objects and advantages of the present invention will be understood by reference to the following detailed description of the invention when considered in combination with the accompanying Figures, in which like reference numerals are used to identify like components throughout this disclosure.

DETAILED DESCRIPTION OF THE PREFERRED EMBODIMENTS

Figure 1:
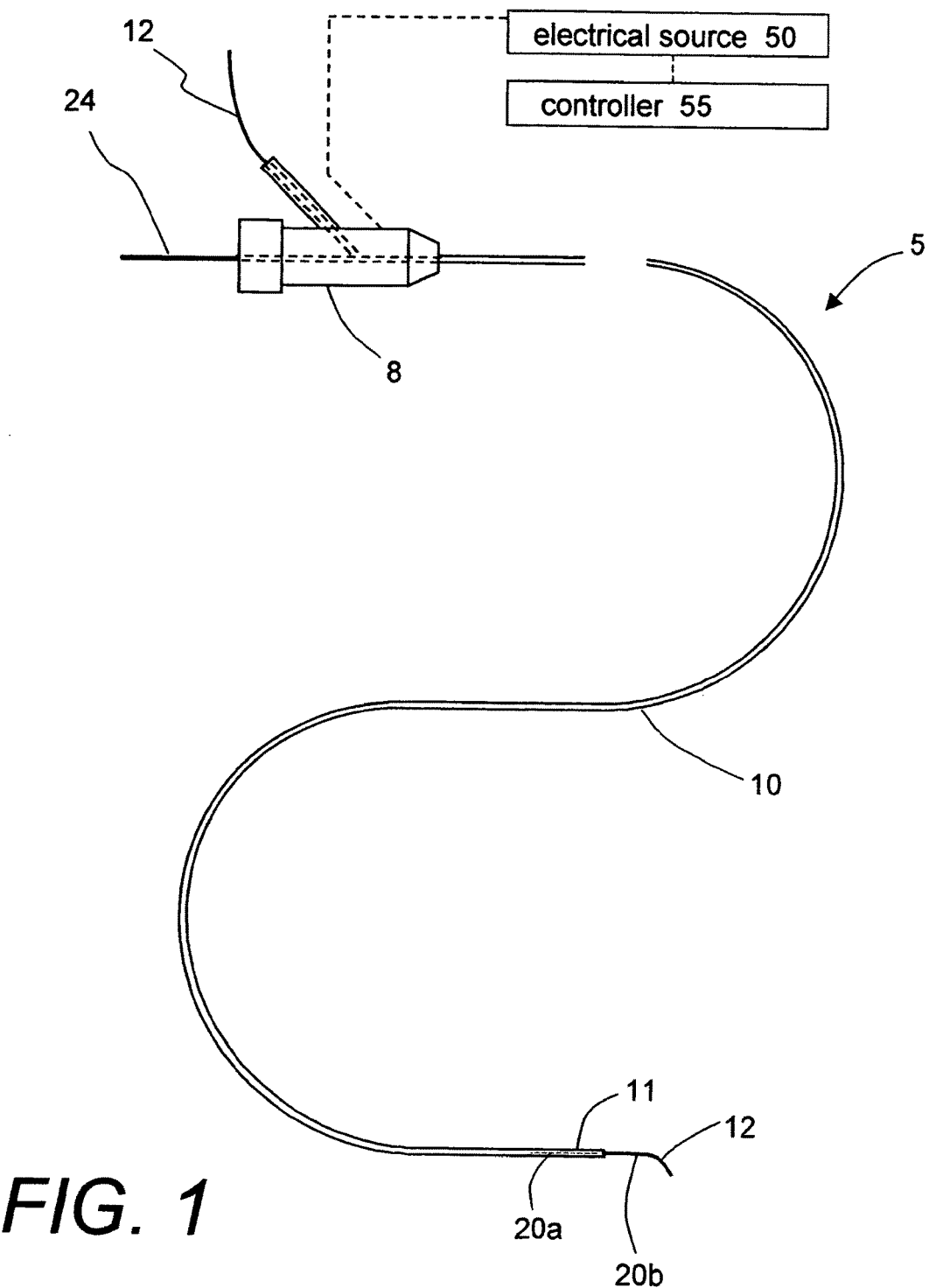
FIG. 1 shows a plan view of Type "A" vaso-occlusive system with an elongate catheter sleeve that carries the polymer embolic element made in accordance with the principles of the present invention.
Figure 2:
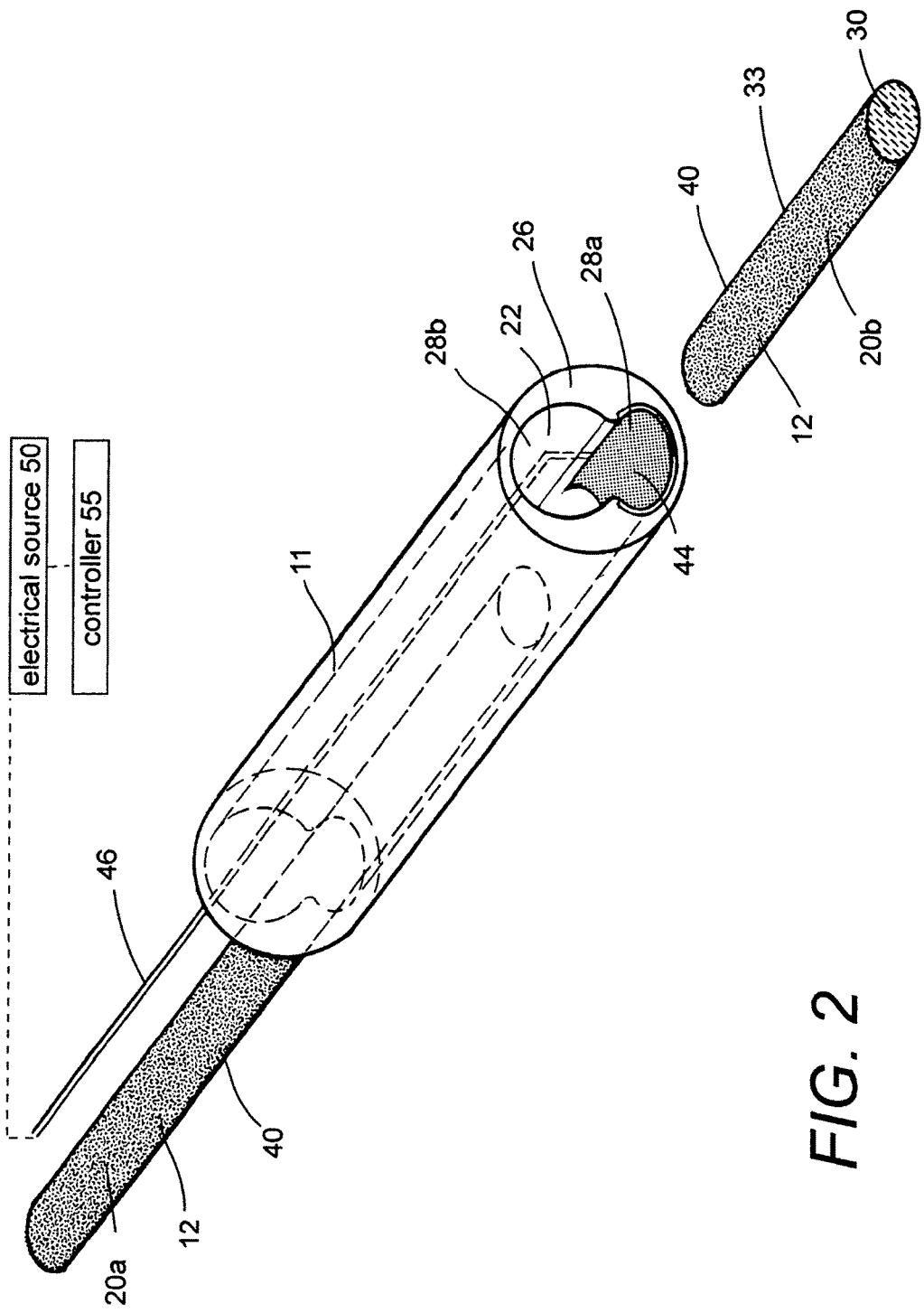
FIG. 2 is an enlarged cut-away view of the working end of the catheter sleeve of FIG. 1 showing an exemplary polymer embolic element with a metallic coating and an electrode arrangement carried within the catheter sleeve.

1. Type "A" embodiment of vascular occlusive system. FIG. 1 shows an elevational view of a Type "A" catheter system 5 for occluding an aneurysm or other vascular malformation. The catheter system has a proximal handle or manifold 8 as is known in the art that is coupled to an elongate microcatheter sleeve 10. FIG. 2 is a cut-away view of the working end 11 of catheter sleeve 10 that illustrates the metallic-coated elongate thread or filament element 12 corresponding to present invention that can be passed axially through the cooperating microcatheter sleeve 10. The flexible embolic element 12 defines a proximal portion 20a still carried within catheter sleeve 10 and a distal thread portion 20b that is pushed outward of the catheter. In this exemplary embodiment, the embolic element 12 has an oval or flattened cross-section, but other cross-sectional shapes are suitable.

Figure 3:
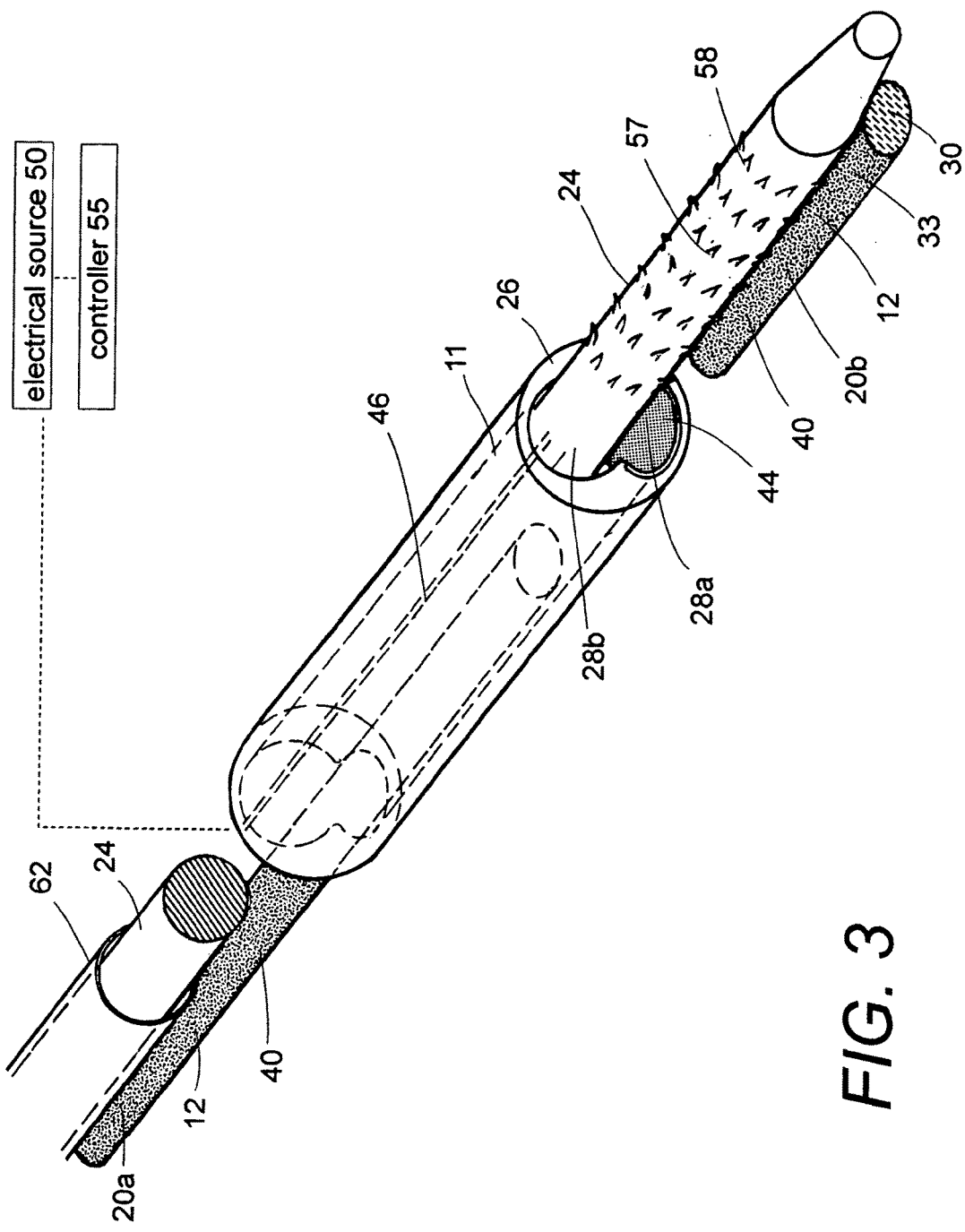
FIG. 3 is a cut-away view of the working end of FIG. 2 with an exemplary extension member adapted for pushing the polymer embolic element member distally from the catheter sleeve.
Figure 4:
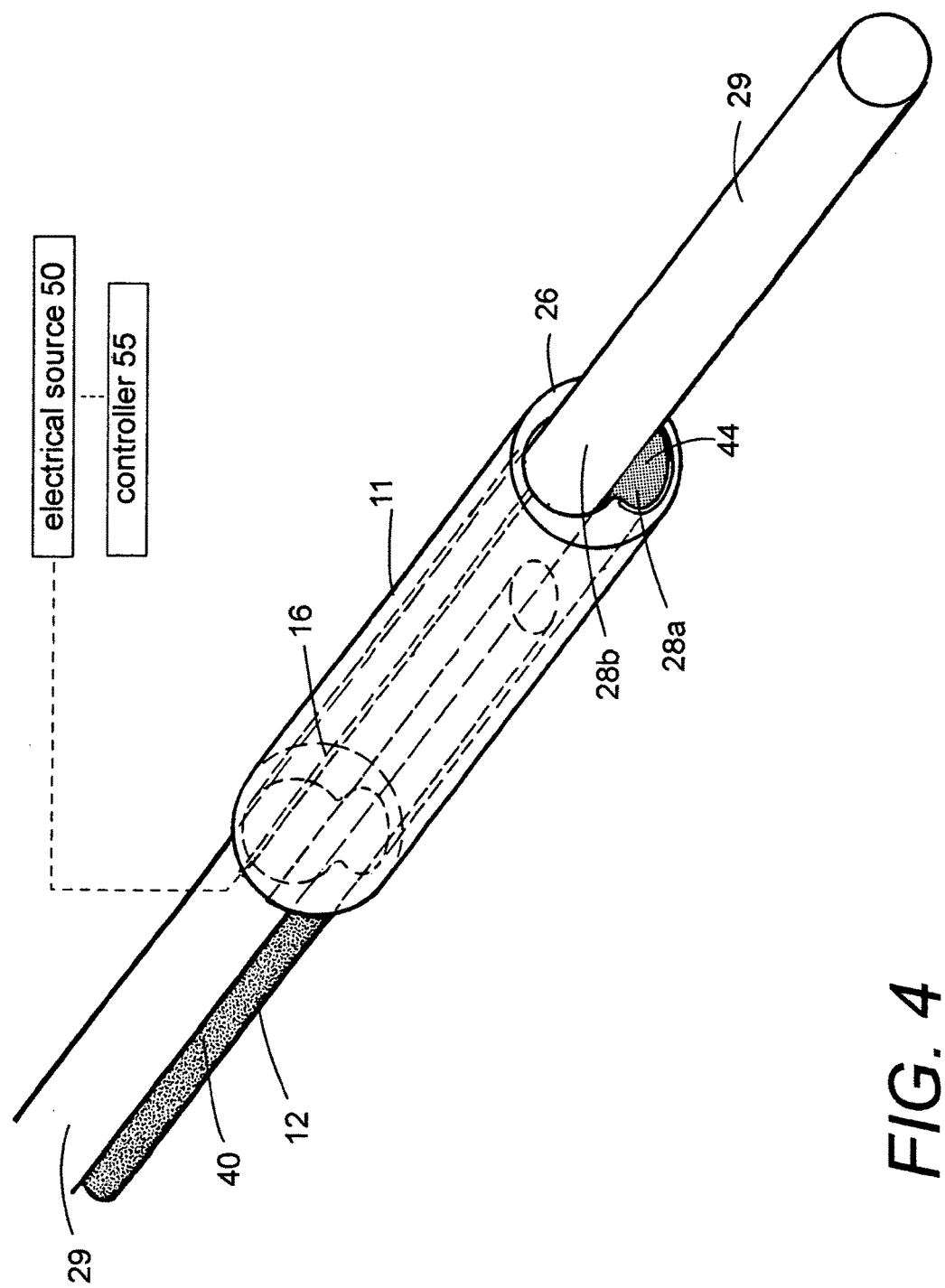
FIG. 4 shows the manner in which the working end of FIG. 2 can be introduced over a guidewire.
Figure 5A:
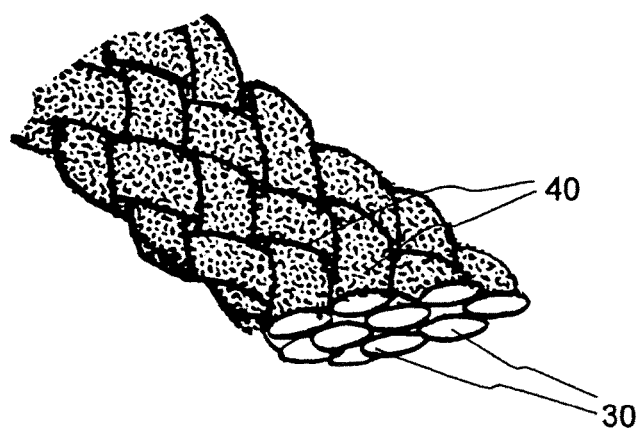
FIG. 5A is view of view of a portion of an alternative embolic element made up of multiple metallic coated filaments.
Figure 5B:
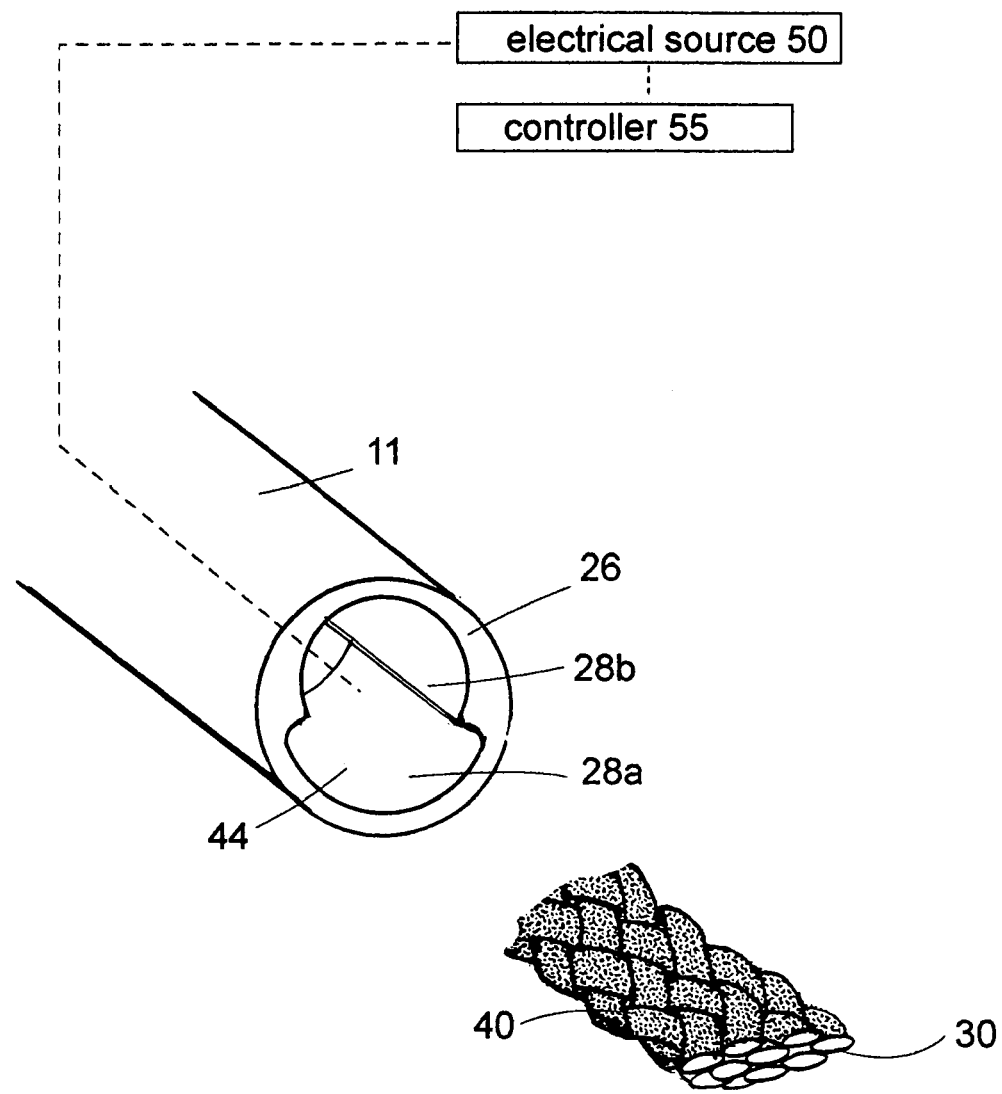
FIG. 5B is a view of the passageway in an alternative embodiment of catheter sleeve that cooperates with embolic element of FIG. 5A.

In this exemplary embodiment, an internal bore or passageway 22 within the catheter sleeve 10 is adapted to carry the embolic thread element 12 as well as to receive a slidable extension member 24 for pushing the polymer thread element 12 from the distal termination 26 of the catheter (see FIG. 3). As can be seen in FIGS. 2 & 3, the cross-sectional form of passageway 22 in the catheter sleeve has a first oval-shape bore portion indicated at 28a for carrying the polymer thread element 12 and a second round-shape bore portion indicated at 28b for slidably receiving the round extension member 24. The second bore portion 28b also is adapted for sliding over a guidewire 29 as shown in FIG. 4. It should be appreciated that the embolic element 12 and cooperating passageway 22 in the catheter sleeve 10 can be formed in several cross-sectional shapes and configurations (e.g., round, flattened and flexible, braided, etc.) and is shown in FIGS. 5A-5B with the embolic element comprising a flattened braid of polymer microfilaments. The cooperating extension member 24 may have and suitable type of mechanism for pushing, pulling, helically advancing, or otherwise expelling the embolic element 12 from distal termination 26 of the catheter sleeve.

Referring now to FIGS. 1 & 2, it is possible to describe several features and characteristics of embolic thread element 12 that adapt it for use in occluding an aneurysm sac or any other vascular malformation. The embolic element 12 has a core 30 of a continuous length of a flexible biocompatible polymeric material, such as nylon, PET, polyamide, aramid fiber, urethane or Kevlar®. The total length of the embolic element or member 12 may range from about 40 cm. to 2000 cm. The cross-sectional dimension of embolic element 12 may range from about 0.0005" to 0.030" in a round cross-section element, or similar cross-sectional area in any rectangular or other sectional shape. A suitable polymer material can be fabricated in an extrusion process, for example, by Polymicro Technologies LLC, 18019 N. 25th Ave., Phoenix, Ariz. 85023-1200. The polymer embolic element 12 further carries a radio-opaque composition as in known in the art (e.g., BaSO.sub.4, BiO.sub.3) to allow fluoroscopic viewing of embolic element 12 as it is maneuvered within a patient's vasculature. The core 30 of the embolic element 12 preferably (but optionally) is somewhat porous thus resulting in an irregular surface indicated at 33 to improve the gripping surface of thin-layer conductive or metallic coating 40 on the embolic element as is described next. FIGS. 5A-5B show an embolic element 12 comprising a plurality of small diameter filaments 42 woven into a flexible braid, with each filament having a metallic coating as described below. A braided embolic element 12 such as depicted in FIG. 5A also would provide a suitable surface 33 for gripping with extension member 24 as described below. It should be appreciated that the flexible embolic element may have a curved or coiled repose shape, and then be straightened as it is passed through the catheter sleeve. Upon deployment, the embolic element would again assume its repose coiled shape to facilitate its introduction into an aneurysm.

As can be seen in FIG. 2, the embolic element 12 carries a thin-layer conductive or metallic coating 40 that has a selected electrical resistivity for accomplishing a method of the invention described below. The metallic coating 40 may be any suitable biocompatible material that can be formed in, or deposited on, the elongate polymeric element 12, such as gold, platinum, silver, palladium, tin, titanium, tantalum, copper or combinations or alloys of such metals, or varied layers of such materials. A preferred manner of depositing a metallic coating 40 on the polymer element comprises an electroless plating process known in the art, such as provided by Micro Plating, Inc., 8110 Hawthorne Dr., Erie, Pa. 16509-4654. The preferred thickness of the metallic coating ranges between about 0.00001" to 0.005". More preferably, the coating thickness ranges between about 0.0001" to 0.001". Still more preferably, the thickness of the conductive coating ranges between about 0.0005" to 0.0007". As will be described below in the Type "C" embodiment, the polymer element also may be extruded with conductive filaments or particles embedded within the polymer matrix of core 30 of the element.

Of particular interest, the combination of the core 30 and metallic or conductive coating 40 of the embolic element 12 provides a selected resistivity to current flow that ranges from about 1 ohm to 500 ohms per 10 cm. length of the embolic element 12 to cause controllable heating about the surface 33 of embolic element 12. More preferably, the element provides a resistivity ranging between about 5 ohms to 250 ohms per 10 cm. length. Still more preferably, the core 30 and conductive coating 40 provide a selected resistivity ranging between about 30 ohms to 60 ohms per 10 cm. length of the embolic element 12.

FIGS. 2 & 3 further illustrate that the distal end of catheter sleeve 10 carries a conductive electrode surface indicated at 44 about a distal region of bore portion 28a that carries embolic element 12. The electrode 44 is coupled to electrical lead 46 that extends within the wall 48 of the catheter to its proximal handle end and to electrical source 50 and controller 55. It should be appreciated that the electrical lead 46 can be a part of a helical braid reinforcement within the catheter sleeve. As can be easily understood by viewings FIGS. 2 & 3, the elongate embolic element 12 can be pushed distally from bore portion 28a, and no matter the axial position of the embolic element, and electrode 44 will substantially contact the metallic surface 40 of the polymer element 12. As will be described below in the method of the invention, the electrical source 50 and electrode arrangement of catheter 10 in combination with the metallic coating of the polymer element 12 are adapted to (i) facilitate rapid occlusion of an aneurysm, and (ii) to sever or divide the polymer thread element 12 to thereby implant any selected length of distal portion 20b of polymer element 12 within in the aneurysm while retaining a proximal length 20a of the polymer element in bore 28a of the catheter. As shown in FIG. 3, the electrode 44 is shown for convenience at the distal end of the catheter sleeve. Preferably, the electrode 44 is spaced slightly inward or proximal from the distal termination 26 of the sleeve to prevent any substantial electrode surface from being exposed to the blood volume proximate to a targeted treatment site.

Figure 5C:
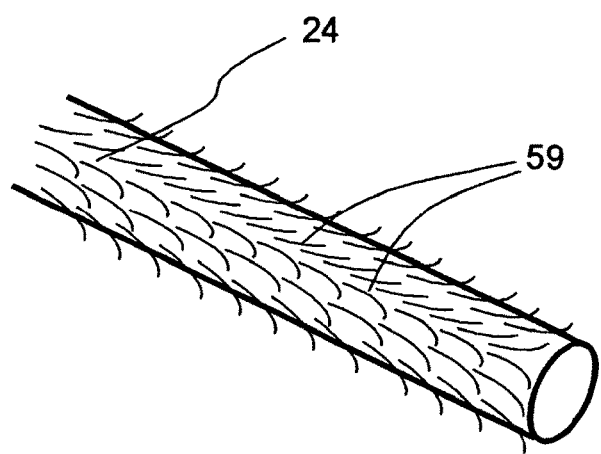
FIG. 5C is a perspective view of an alternative embodiment of extension member adapted to grip the embolic element.

In the system shown in FIGS. 2 & 3, the exemplary polymer element 12 is very soft and flexible, for example, having the flexibility characteristics of a common thread or suture. In order to deploy the polymer thread element 12 from distal termination 26 of catheter sleeve 10, this embodiment utilizes a slidable extension member 24 that has unidirectional gripping elements 57 (herein alternatively called barbs) about a distal region 58 of the extension member 24. As can be understood in viewing FIG. 2, an axial movement or projection of extension member 24 from sleeve 10 will cause the barb elements 57 to grip the embolic element and pull it from bore portion 28a. When the extension member 24 is moved proximally in bore portion 28b, the barb elements will slide over surface 33 of embolic element 12 thus leaving a selected length of the embolic element disposed outside distal termination 26 of the catheter sleeve. The barb or gripping elements 57 may be provided in extension member 24 may comprise cuts into the surface of a polymer extension member 24. Alternatively, the gripping elements may comprise a fiber or other type of hair-like filament 59 bonded to the surface of an extension member 24 as shown in FIG. 5C.

The catheter sleeve 10 while carrying the polymer embolic element in bore portion 28a may be introduced into vasculature over a guidewire 29 as shown in FIG. 4. The guidewire then can be removed and be replaced by the extension member 24. To facilitate the slidable introduction of the extension member 24 and grip elements into bore portion 28b while embolic element 12 is carried within bore portion 28a, the extension member may cooperate with a very thin-wall sleeve 62 of Teflon® or any other suitable material to prevent the gripping elements 57 from gripping the embolic element 12 as the guidewire is replaced with the extension member 24. As can easily understood from viewing FIG. 3, to expose the distal portion 58 of the extension member 24 and gripping elements 57, the thin-wall sleeve 62 can be retracted from the gripping elements by pulling it proximally at the handle 8 of the catheter.

The system 5 further provides feedback control mechanisms within controller 55 for modulating energy delivery to electrode 44 and thereby to the conductive component of the embolic element. Referring again to FIG. 3, at least one thermocouple 88 is provided at either surface of electrode 44 to measure the temperature of the electrode which is substantially the same as the surface temperature of the embolic element in contact therewith. The thermocouple 88 is linked to controller 55 by an electrical lead (not shown). The controller 55 is provided with software and algorithms that are adapted to modulate power delivery from electrical source 50 to maintain the temperature of the embolic element (or electrode 44) at a particular level or within a particular temperature range, in response to feedback from the sensor.

Figure 6A:
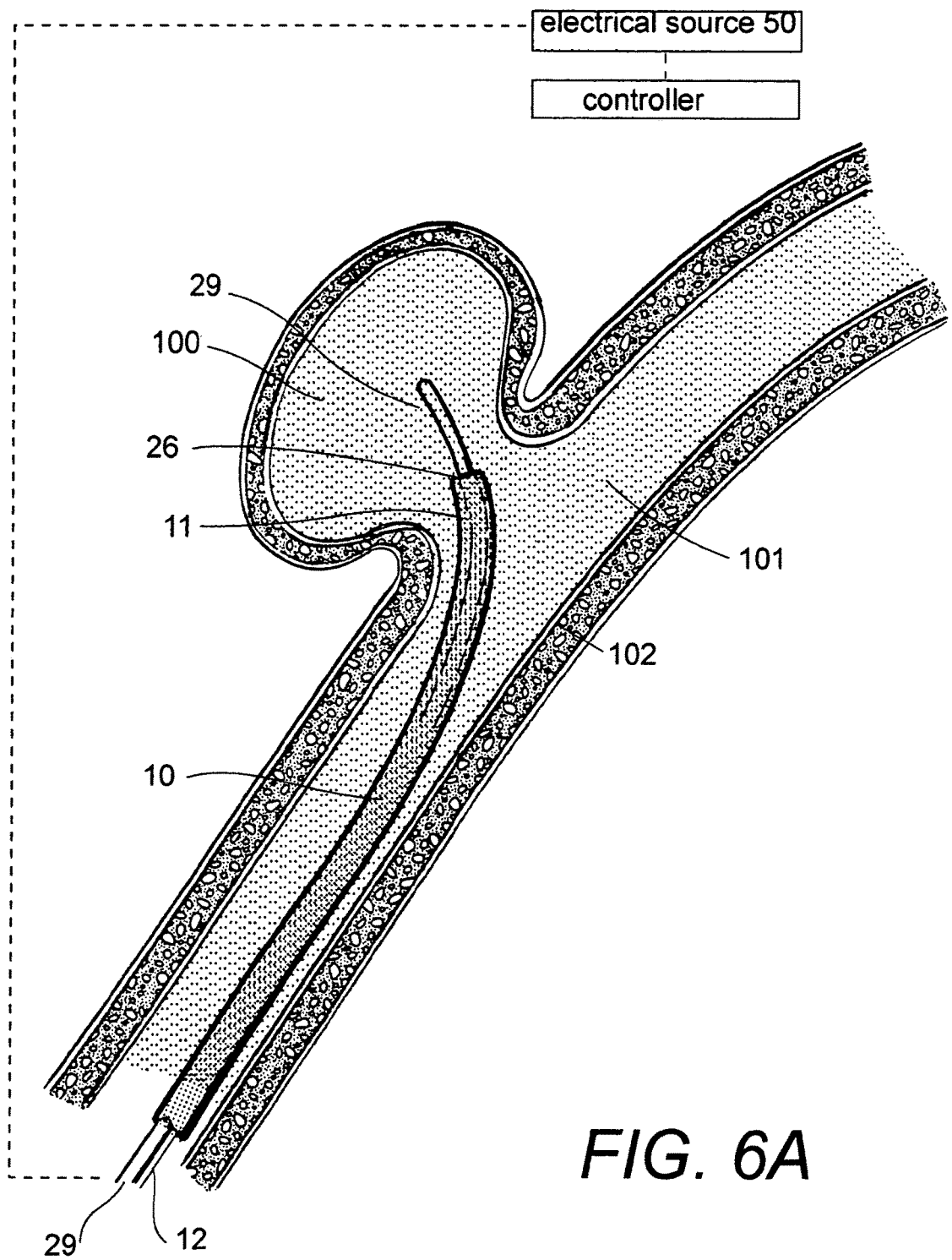
FIG. 6A is a view of the working end of the Type "A" system of FIGS. 1 & 2 disposed in a blood vessel proximate to an aneurysm.
Figure 6B:
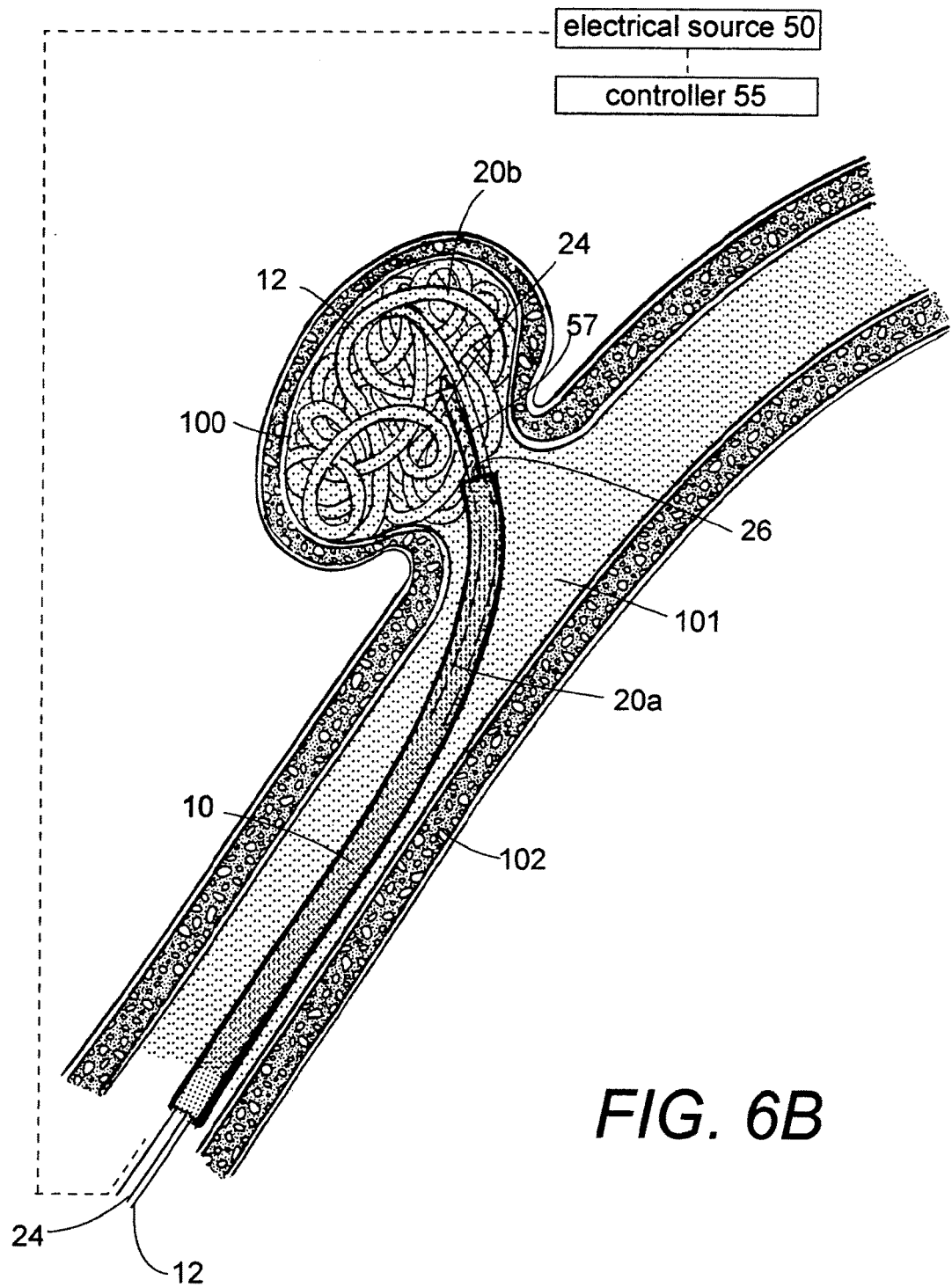
FIG. 6B is a view of the working end of FIG. 6A after a selected length of a distal portion of the polymeric member is disposed in the aneurysm and formed into a tangled mass to occupy a volume of the aneurysm.

Now turning to FIGS. 6A-6B, the manner of using the catheter system 5 to introduce the polymer embolic element 12 into a cerebral aneurysm indicated at 100 or any other targeted vascular site is shown. In FIG. 6A, it can be seen that working end 11 of catheter sleeve 10 is introduced through blood 101 flowing in vessel 102 until its distal termination 26 is positioned adjacent to, or partially within, the aneurysm 100. Typically, the catheter is guided to the aneurysm over guidewire 29 that is accommodated by bore portion 28b of the catheter sleeve (see FIGS. 4 & 6A). In FIG. 6B, it can be seen that guidewire 29 has been withdrawn from catheter passageway 28b, and thereafter the extension member 24 has been introduced back through the same passageway. The (optional) thin-wall sleeve 62 as shown in FIG. 3 is withdrawn to expose gripping elements 57 at distal portion 58 of the extension member. FIG. 6B depicts an elongate distal portion 20b of the embolic element 12 being disposed in the aneurysm sac 100 which has been caused by pushing the extension member 24 to and for thereby causing the grip elements 57 to engage surface 33 of embolic element 12 and successively carry small axial lengths of element 12 distally into the aneurysm under fluoroscopic control. In this manner, any selected length of distal portion 20b of polymer element 12, for example from about 5 cm. to 200 cm. for a typical aneurysm, can be fed into the malformation. The selected length and volume of embolic element 12 thereby displaces blood 101 and occupies a selected (first) volume of the vascular malformation.

As can be seen in FIG. 6B, the volume of aneurysm 100 can be substantially occupied with the embolic element 12, depending on its flexibility, to accomplish a first aspect of the method of the invention. In effect, the embolic element 12 causes an initial partial mechanical occlusion of the aneurysm volume by implanting a selected volume of occlusive material (i.e., the entangled length of polymer element 12) within the aneurysm which displaces a similar volume of blood 101 and thereby slows blood flow through the aneurysm and pressure therein. Next, a second novel aspect of the method of the invention is practiced wherein electrical energy is controllably delivered to embolic element 12 to increase the volume of occlusive material within the aneurysm by adding a layer of coagulum 104 about the polymer embolic element 12 thereby occupying a second volume of the aneurysm.

Figure 6C:
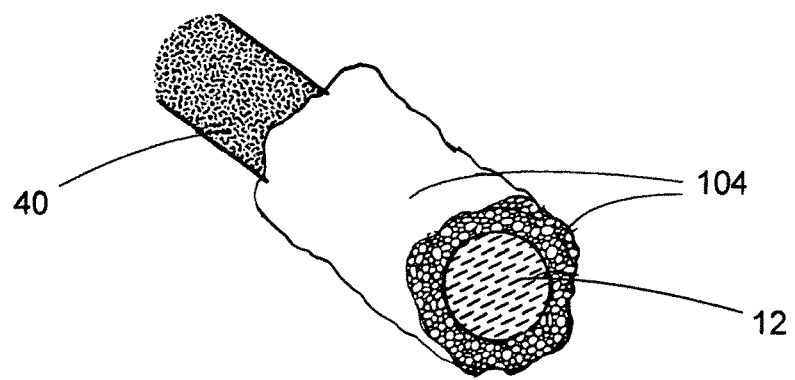
FIG. 6C is a graphic view of portion of a polymer embolic element with coagulum formed around the element by resistive heating of the metallic surface to increase the volume of occlusive material within a malformation.

More in particular, referring to FIGS. 6B & 6C, after the selected length of distal portion 20b of polymer element 12 is fed into aneurysm 100 under fluoroscopic control, the physician actuates the electrical source 50 via controller 55 to deliver electrical energy to electrode 44. The contact between electrode 44 and metallic surface 40 of polymer element 12 causes current flow along the metallic surface 40 of the entangled element and within the patient's body to a return electrode such as a ground pad in contact with the patient's body. The selected resistivity designed into the combination of metallic coating 40 and embolic element core 30, as described above, causes resistive heating of the element 12. The temperature of the surface 33 of the embolic element (as well as slight active ohmic heating of blood about the element 12) causes denatured blood products and coagulum to adhere about surface 33 of the embolic element. As depicted graphically in FIG. 6C, the thermally-induced coagulation of blood 101 causes a substantial layer of coagulum 104 to form around the embolic element 12 to thus provide a greater volume of occlusive material within the aneurysm 100. In a preferred mode of operation, the thermocouple 33 (see FIG. 3) together with feedback circuitry to the controller 55 are used to modulate power delivery to electrode 44 to maintain the embolic element at the catheter terminus at a pre-selected temperature level for a selected period of time. The method of invention maintains the surface temperature of embolic element 12 within a range of about 45.degree. C. to 100.degree. C. More preferably, the surface temperature of the embolic element is maintained within a range of about 65.degree. C. to 90.degree. C. to create the desired coagulum. This aspect of the method of the invention thus increases the volume of occlusive material within the vascular malformation to further mechanically reduce blood circulation within the defect. Thereafter, the occlusive material (embolic element and coagulative layer) within the aneurysm then rapidly will cause accumulation of platelets and other clotting factors about the occlusive material to complete the occlusion of the aneurysm volume as a result of the body's wound healing response to the occlusive material volume within the aneurysm 100.

In accomplishing the above-described method of the invention, the electrical energy delivery provided by source 50 and controller 55 can be in the radiofrequency range and at a first power level ranging between about 1 watt and 50 watts. More preferably, the power level ranges between about 5 watts and 15 watts. It is proposed that current flow for about 5 seconds to 1200 seconds will cause the desired thickness of coagulative material to form around the embolic element 12 to assist in the mechanical occlusion of an aneurysm or other vascular defect. It should be appreciated that the duration of power delivery is a factor in creating a desired thickness of coagulative material on the embolic element. However, the process of causing the formation of a coagulative layer about the embolic element is essentially self-terminating, which adds to the safety of practicing the method of the invention. The method is self-terminating in the sense that as the coagulative layer builds to the desired selected thickness, the layer serves as an insulative layer and thereby prevents further denaturation of blood compositions (or ohmic heating of blood proximate to the embolic element.

The method of using an embolic element having a resistivity in the selected range described above has the advantage of preventing any possibility of creating energy densities ("hot spots") within the aneurysm wall that could perforate the aneurysm sac. The low power levels utilized in this method of the invention can easily cause resistive heating of the metallic surface coating 40 for coagulation purposes, but cannot cause significant localized current flows (i.e., energy densities) that could perforate a vessel wall, or create energy densities that could cause ohmic heating of collateral brain structure. Of particular importance, the thermally-induced coagulative process is effectively self-terminating since the temperature level at surface 33 of the metallic coating 40 will become insulated by the coagulum, thus preventing overheating of the interior or the aneurysm.

Figure 7:
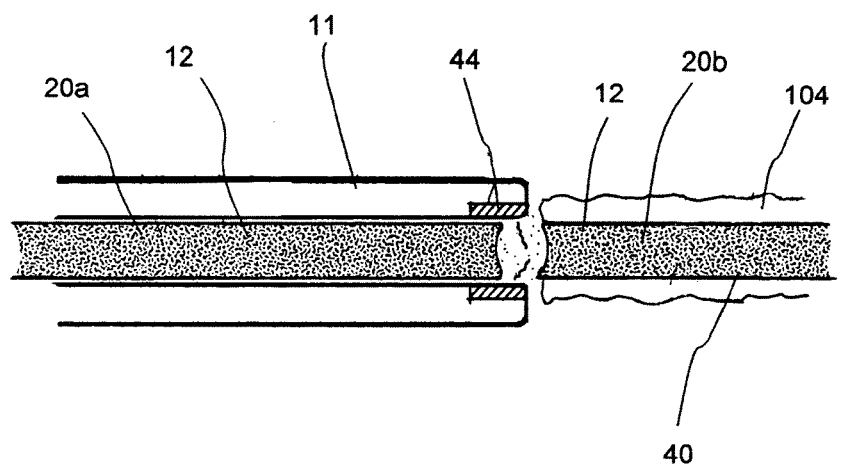
FIG. 7 is a graphic view of a manner of practicing a method of the invention in utilizing a selected level of electrical energy to divide the implanted embolic element from a proximal portion of the polymeric element still within the catheter sleeve.

FIG. 7 graphically illustrates the next step of the method of the invention that involves separation of the distal portion 20b of embolic element 12 entangled within aneurysm 102 (see FIG. 6B) from proximal portion 20a of embolic element 12 still within the catheter sleeve 10. In order to accomplish the separation of the embolic element 12 according to the invention, the physician actuates electrical source 50 via controller 55 to deliver current flow to electrode 44 that has a selected second (higher) power than the previously described power levels. As can be understood in FIG. 7, the insulative coagulum around the embolic element 12 will substantially prevent current flow at the second higher power level to course through the endovascular media, thus eliminating the possibility of high localized current densities. However, at the interface 107 between electrode 44 and metallic surface in contact with the electrode, the current flow will create a transient high energy density in and about metallic coating 40 and core 30 of element 12 to cause thermal melting of the polymer core to thereby divide the embolic element 12. To divide the embolic element, it is believed that a power level ranging between about 5 watts and 100 watts is suitable. More preferably, the power level is within the range of about 10 watts to 30 watts. It is believed that current flow for about 0.01 seconds to 20 seconds will divide the embolic element. Following the division of the implanted embolic element 12, the catheter 10 that carries the proximal portion 20a of the embolic element is withdrawn from the patient's vasculature.

The previously described means of dividing the embolic element with electrical energy has the particular advantage of allowing the physician to implant any desired length of the embolic element 12 within an aneurysm or other vascular defect. The physician simply can advance a length the polymer element into the defect under fluoroscopy until the entangled volume appears optimal, and then deliver electrical energy at the first and second power levels to (i) add coagulative volume to the occlusive material in the vascular defect, and then (ii) to separate the implanted embolic element 12 from the remainder of the element still within the catheter. This method of the invention, of course, can be practiced for implanting an embolic element without utilizing electrical energy to add a coagulative layer to the embolic element as described above.

In another embodiment of embolic element 12, the polymer or the metallic coating is formed in a coiled or curved shape and the material has a memory of such a curved shape. The flexible embolic element 12 then conforms to a generally linear configuration for feeding through a catheter sleeve. Upon deployment beyond the distal terminus of the catheter sleeve, the embolic element then will substantially assume its curved or coiled shape which will assist in its insertion into an aneurysm.

Figure 8:
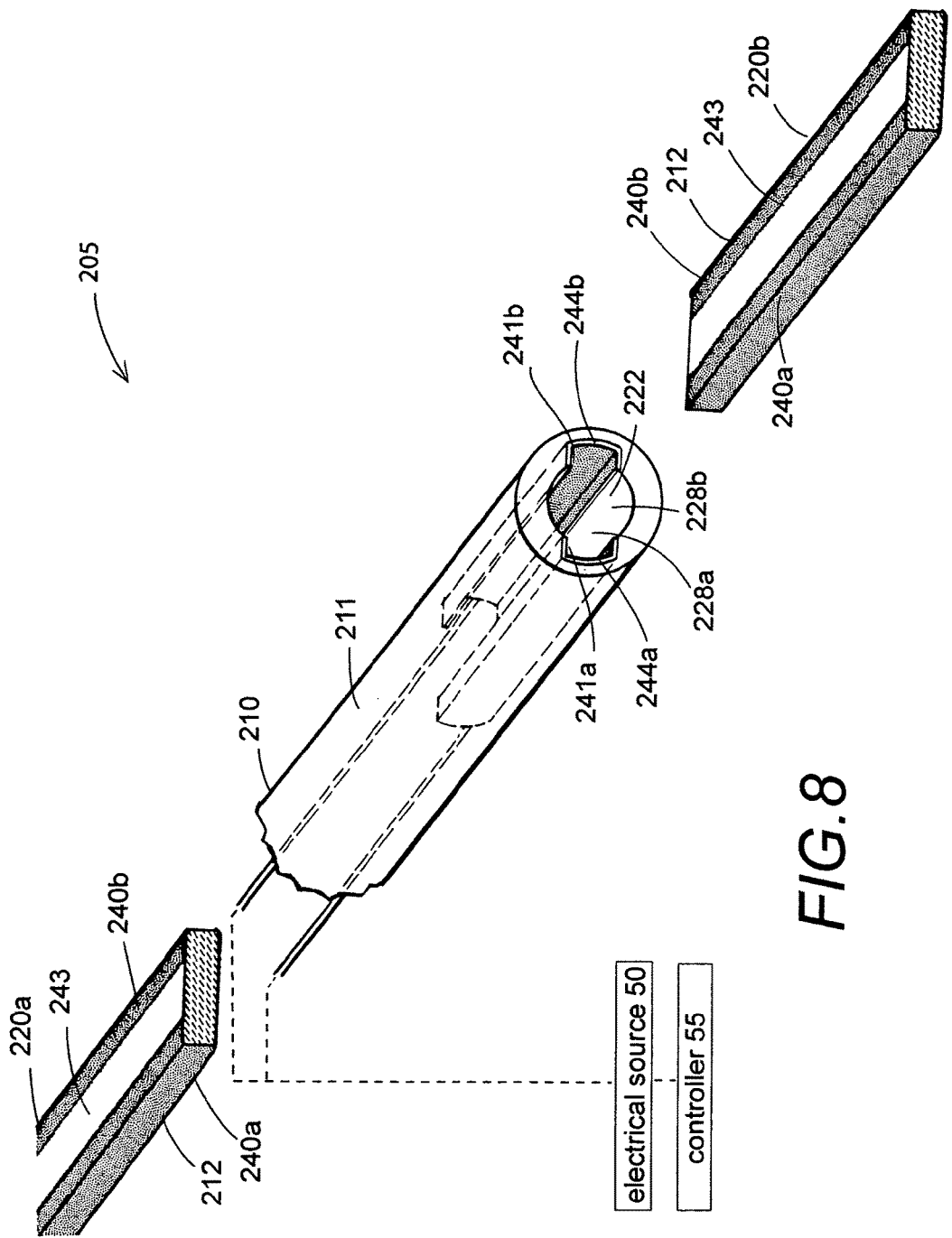
FIG. 8 is a cut-away view of the working end of Type "B" vaso-occlusive system showing a polymer embolic element with first and second spaced apart metallic coatings made in accordance with the principles of the invention.

2. Type "B" embodiment of vaso-occlusive system. FIG. 8 shows a cut-away view of a Type "B" catheter system 205 for occluding an aneurysm, other vascular defect or malformation or any targeted site within a patient's vasculature. The catheter system is similar to the previously described embodiment and has a proximal handle or manifold 8 coupled to an elongate microcatheter sleeve 210 that terminates in working end 211. As can be seen in FIG. 8, this system comprises a metallic-coated elongate member 212 that can be passed axially through cooperating bore 222 in the microcatheter sleeve 210. This Type "B" system differs from the previously disclosed system in that the flexible continuous embolic member 212 (that defines proximal portion 220a and distal thread portion 220b) functions in two alternative manners: (i) the flattened embolic member 212 is substantially stiffened to allow it to be pushed outward from a handle end 8 of the catheter sleeve without requiring a pushing member or extension member as described above, and (ii) the polymer embolic member 212 carries first and second spaced apart metallic coating portions to act as resistive elements and to further act as a bi-polar delivery system to perform alternative methods of the invention in creating coagulative material and in dividing the polymer embolic member 212 after implantation in a vascular malformation.

In this exemplary Type "B" system embodiment, the internal bore 222 is shaped to receive the flattened embolic thread member 212 in a rectangular shaped bore portion indicated at 228a. Additionally, the catheter sleeve is adapted to slide over a round guidewire (not shown) that is accommodated by the round shape bore portion 228b. In this embodiment, the embolic thread member 212 again has a body core 230 of a continuous length of a flexible polymeric filament. The polymer embolic member 212 again carries a radio-opaque composition.

As can be seen in FIG. 8, this alternative embodiment of embolic member 212 carries first and second opposing thin-wall metallic coating portions 240a and 240b that extend the length of the embolic member 212. The metallic coating in this embodiment again has a selected resistivity to current flow that ranges from about 1 ohm to 500 ohms per 10 cm. length, although a lesser resistivity also is functional for some methods of the invention. For example, the opposing metallic coating portions 240a and 240b can act as bi-polar electrodes as will be described below. In such an application, the first and second metallic portions 240a and 240b extends along first and second sides 241a and 241b of the entire length of the embolic member 212. It can be seen that these first and second metallic surfaces define a center-to-center dimension and can act as bi-polar electrodes, since the surface portions are spaced apart on either side of a medial non-metallic surface portion indicated at 243.

FIG. 8 further illustrates that working end 211 of catheter sleeve 210 carries spaced apart first and second conductive electrodes 244A and 244B on either side of bore portion 228a that carries embolic member 212. The electrodes 244A and 244B are coupled to electrical leads 246a and 246b in wall 248 that extend to electrical source 50 and controller 55. As can be understood by viewing FIG. 8, the elongate polymer member 212 is substantially stiff so that it can be pushed distally from bore portion 228a from the handle end of the catheter, and the electrodes 244A and 244B will always be in contact with the respective metallic surface portions 240a and 240b of the polymer element 212. Alternatively, the embolic member can be pushed distally by an extension member as described previously.

The manner of using catheter system 205 to perform the methods of occluding a cerebral aneurysm 100 can be easily described, still referring to FIG. 8. The elongate polymer member 212 is passed through the catheter sleeve 210 and thereby fed into the aneurysm 100 similar to the graphic representation of FIG. 6B. Thereafter, a guidewire (if used) is withdrawn from the catheter passageway 228b. Thus, the aneurysm sac can be substantially occupied with embolic member 212 to partially mechanically occlude the aneurysm volume.

Next, the physician actuates electrical source 50 via controller 55 to deliver electrical energy to common polarity electrodes 244A and 244B. The contact between electrodes 244A and 244B and the metallic surface portions 240a and 240b of embolic member 212 causes current flow along the metallic surfaces of the entangled member in cooperation with a return electrode such as a ground pad. The selected resistivity of the metallic surface portions 240a and 240b of polymer element 212 then will coagulate blood about the surface of the embolic member 212, generally as described previously to add to the volume of implanted occlusive material.

In a more preferred method of operation, the electrical source 50 and system 205 is provided with circuitry that allows controller 55 to programmably deliver bi-polar Rf current at a first power level to electrodes 244A and 244B which are in contact with the opposing metallic surface portions 240a and 240b of polymer member 212 to cause current flow between the metallic surface portions 240a and 240b. This manner of bi-polar current flow is advantageous since it will not cause high current densities in any endovascular media that might then threaten perforation of the aneurysm wall. Such bi-polar flow thus will rapidly cause a coagulative layer on the embolic member (generally between the metallic surface portions 240a and 240b) to thereby add to the volume of occlusive material within the aneurysm. In using the paired metallic surface portions 240a and 240b in such a bi-polar energy delivery modality, the metallic coatings may provide any lesser resistivity to current flow for performing the method of the invention.

In another energy delivery modality, the controller may sequence delivery of mono-polar Rf current to the working end 211 in cooperation with a ground pad and bi-polar flow between the paired metallic surface portions 240a and 240b to cause coagulum to form about the embolic member 212. The system further may use a thermocouple (not shown) and feedback circuitry as described above to maintain the surface of the embolic member within the desired temperature range as described above.

The use of the paired metallic surface portions 240a and 240b in a bi-polar mode is particularly adapted for use in the next step of the method of the invention that involves separation of the distal portion 220b of embolic member 212 entangled within aneurysm 102 (cf. FIG. 6B) from proximal portion 220a still within catheter sleeve 210. In using this embodiment, the physician actuates electrical source 50 via controller 55 to deliver bi-polar Rf current flow between electrodes 244A and 244B at a selected second (higher) power level than used in the coagulation modality. In this case, the second power level causes the core 230 of embolic member 212 to resemble a fuse as the current courses between the electrodes to thus divide embolic member 212 at the distal termination 226 of the catheter sleeve. It is believed that the method of using bi-polar Rf current flow between paired electrodes will allow separation of the embolic member 212 within a range of about 0.1 to 10 seconds. Again, this embodiment of the invention then allows any suitable length of embolic member 212 to be introduced into the aneurysm—and then separated at the catheter end.

In another Type "B" embodiment, the emboli member may have a transverse section in the shape of a "C" (not shown) to partially wrap around a guidewire or a pusher member (see FIG. 3). It can be easily understood that such a cross-sectional shape would allow the "C" shape to function in the fashion of rapid-exchange catheter systems as are known in the art to insert over a guidewire. Further, this embodiment would allow bi-polar electrode surfaces on opposing and spaced apart inner and outer surfaces of the embolic member to otherwise function as described above.

Figure 9:
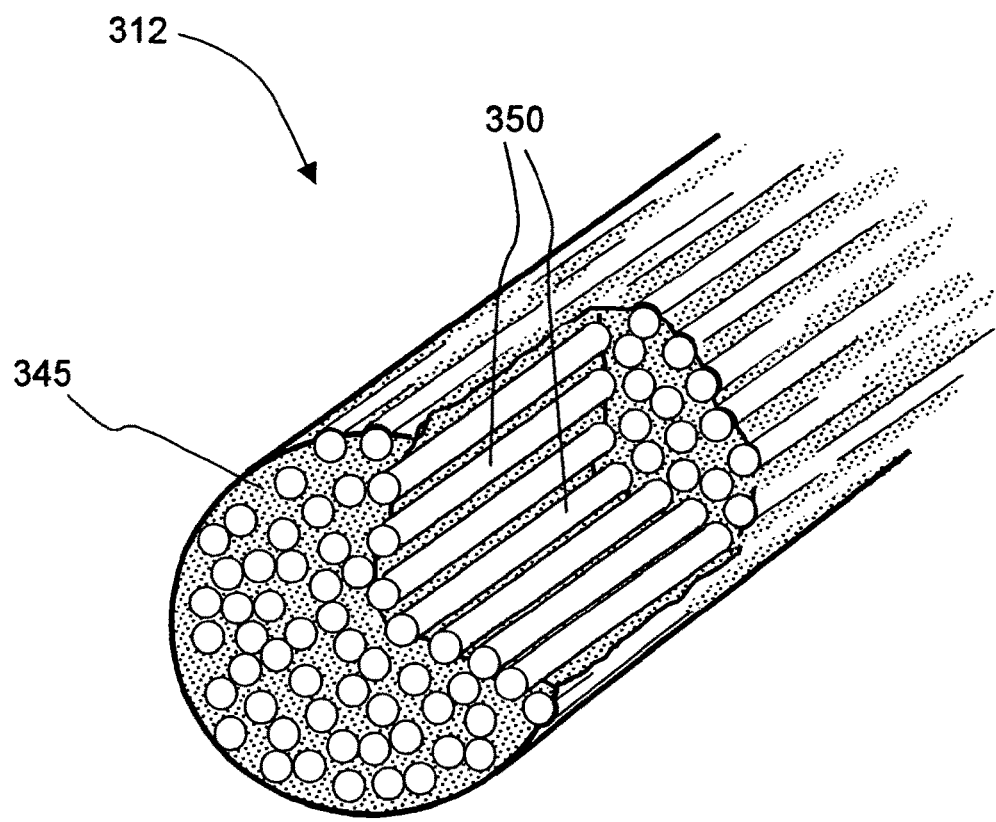
FIG. 9 is a sectional view of an embolic element of a Type "C" vaso-occlusive system wherein the embolic element comprises a matrix of a polymer with conductive microfilaments embedded therein.
Figure 10:
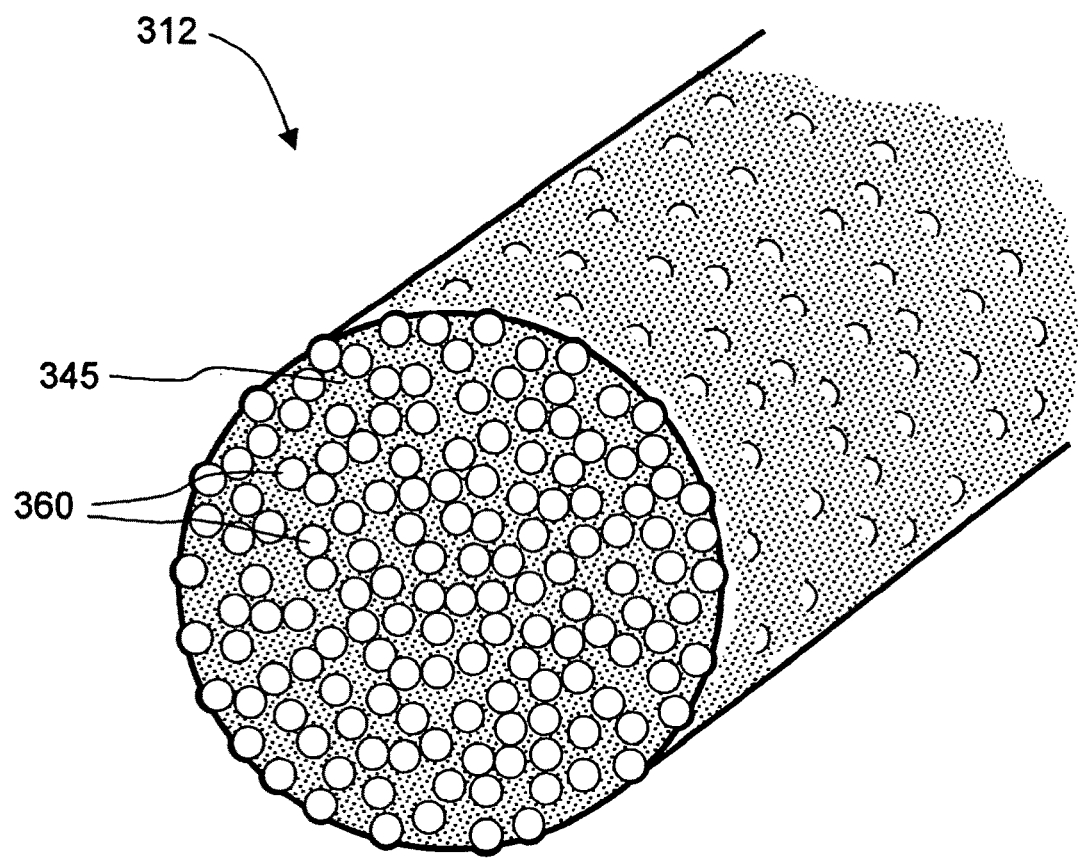
FIG. 10 is a sectional view of an alternative embolic element of a Type "C" vaso-occlusive system wherein the embolic element comprises a matrix of a polymer with conductive particles distributed therein.

3. Type "C" vaso-occlusive system. This alternative Type "C" system uses a catheter sleeve as described in the Type "A" embodiment above. This system differs only in the construction of elongate embolic member 312 shown in FIGS. 9 and 10. The flexible continuously extruded embolic member 312 again comprises a substantially polymer core together with a conductive component that provides the member with a specified resistivity. In one alternative embodiment of Type "C" embolic member shown in FIG. 9, the member 312 comprises a polymer matrix 345 that is co-extruded with micro-filaments 350 of any suitable conductive material embedded therein, such as tungsten, stainless steel or carbon fiber. The micro-filaments 350 can be partially exposed at the surface of the member to contact the electrode arrangement carried at the distal termination of the catheter sleeve. In another alternative Type "C" embolic member shown in FIG. 10, the member 312 comprises a polymer matrix 345 with embedded particles 360 of any suitable conductive material to thereby provide the resistivity specified above. The polymer conductive-resistive matrix of embolic member 312 functions as a fuse to divide the embolic member at the distal end of a catheter as described in the Type "A" embodiment.

Figure 11:
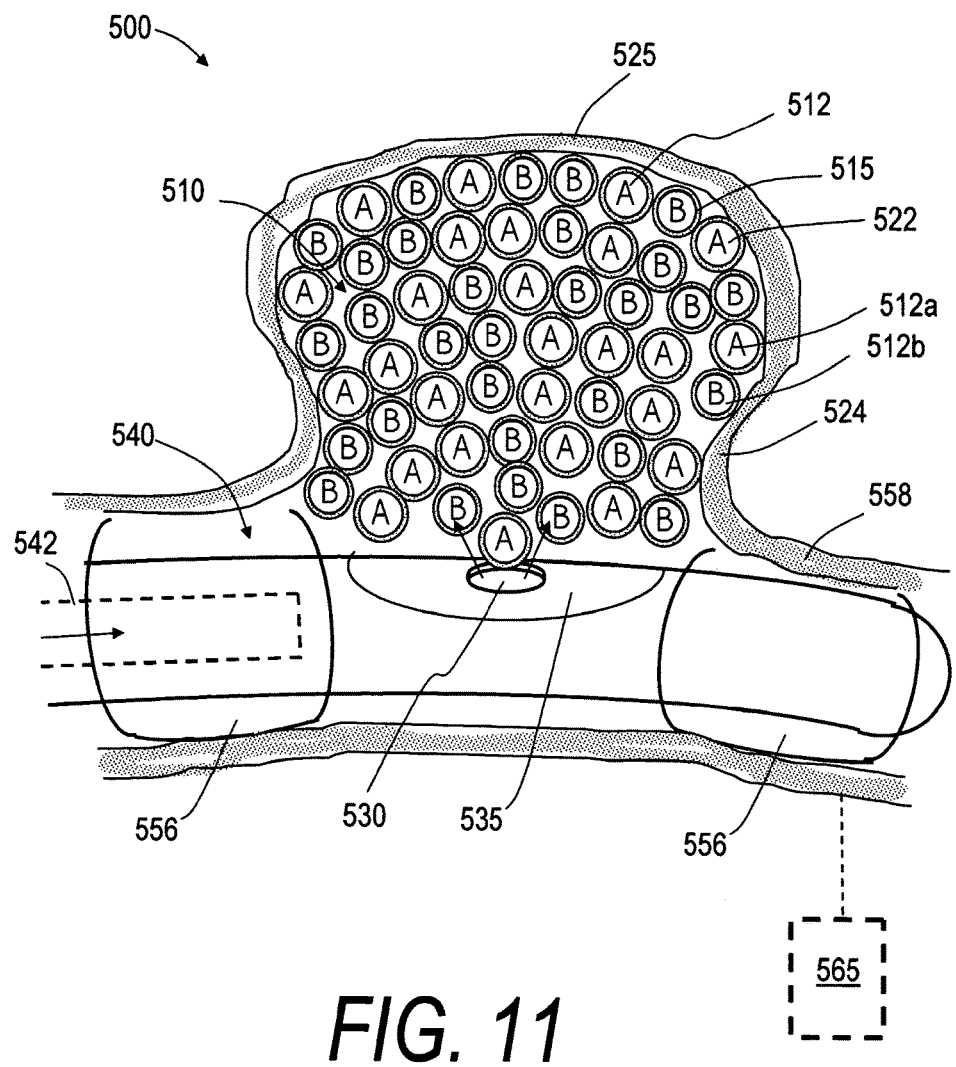
FIG. 11 is a schematic view of an alternative Type "D" vaso-occlusive system and a first step in its method of use wherein a catheter working end introduces a binary media of microspheres with sacrificial shells into an aneurysm sac.

4. Type "D" vaso-occlusive system. FIG. 11 provides a schematic illustration of an exemplary Type "D" vaso-occlusive system 500 that is adapted to fill an aneurysm sac with novel media 510 corresponding to the invention that can be altered from a first flowable state to a second more solidified state. The system and media 510 are directly related to the conductive-resistive polymer matrix described in the Type "C" embodiment above.

In FIG. 11, the system of the invention is shown schematically wherein a binary system of biocompatible agents are encapsulated in microspheres 512 (collectively). The microspheres have an exterior sacrificial shell portion indicated at 515 that is of a conductive matrix material as described previously. The interior or cores 522 of the hollow microspheres 512 comprise either a fast or second composition (indicated at "A" or "B" in FIG. 15) that when mixed together cause a polymerization process between the compositions that will alter the media 510 from a flowable media to a substantially non-flowable media, e.g., a solid or stiff gel-like material. Thus, the media 510 in its flowable state—with first and second types of microspheres therein—can be introduced into an aneurysm from an opening in the distal termination of a catheter, or from a port 530 in the side of the catheter's working end. Any type of pusher mechanism can be used to expel the flowable media 510 from the catheter. Preferably, the flowable media 510 carries radio-opaque materials or any other material that can cooperate with an imaging system to allow the physician the ability to view the introduction of the media into an aneurysm 525 (FIG. 11).

The sacrificial shell portions 515 of the microspheres can be of a degradable material similar to materials described previously that have conductive particles distributed therein. In one embodiment, the polymer shell material 515 carries particles that can generally be described as "radiosensitive" in that they respond to electromagnetic energy of a selected frequency. Thus, the catheter corresponding to the invention can carry energy deliver means for reducing, degrading, melting, disintegrating or otherwise fracturing the sacrificial shell portions 515 of the microspheres. In one embodiment, the sacrificial shell can be a wax or lipid with radiosensitive particles therein that can be elevated in temperature (i) by resistive heating due to current flow from an electrode 535 on the catheter working end or (ii) by inductive heating from an emitter electrode as is known in the art.

Thus, the invention provides a vaso-occlusive system that comprises a flowable media 510 that carries a volume of microspheres 512 of first and second types, wherein each type of microsphere has a sacrificial shell 515 that surrounds an interior core portion 522. The core portions, when allowed to interact, form a binary system for polymerizing the media 510 into a non-flowable gel or a solid.

Now turning to FIG. 11, the distal working end 540 of a catheter is shown schematically as being introduced to the region opposing the neck 524 of an aneurysm 525. A pusher 542 is used to expel a volume of media 510 from the port 530 which is directed into the aneurysm. The axial movement and angular rotation of the catheter is assisted by suitable markings on the catheter that cooperate with an imaging system. During navigation of the catheter, the port 530 can be maintained in a closed state by a slidable cover, or by a burstable film or the like. The volume of media 510 in FIG. 11 is illustrated for convenience with "A" and "B" particles (indicated at 512a and 512b) that are grossly out of scale. In practice, the microspheres can have a dimension across a principal axis thereof ranging between about 10 nanometers and 100 microns. More preferably, the microspheres have a dimension across a principal axis ranging between about 100 nanometers and 100 microns. FIG. 11 further shows that the catheter working end 540 carries an optional balloon system 556 for engaging the walls 558 of the blood vessel to insure that all of the media 510 is directed into the aneurysm sac.

Figure 12:
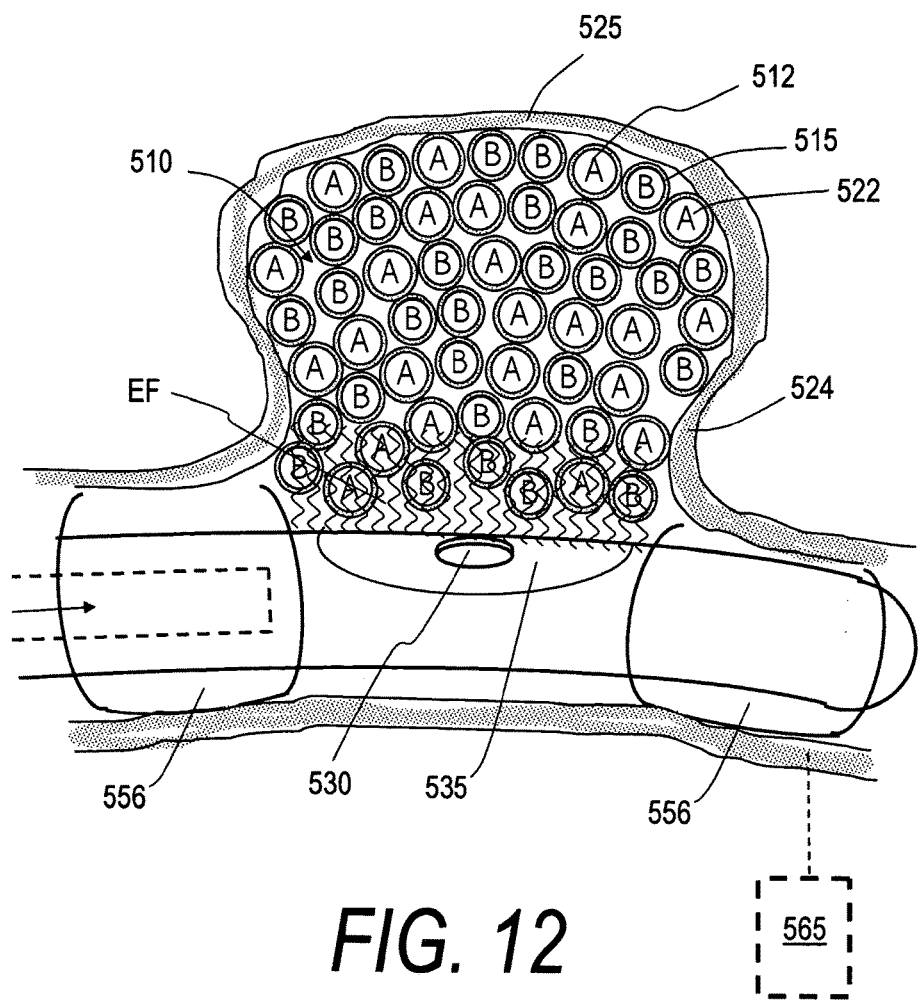
FIG. 12 is a schematic view of another step in utilizing the vaso-occlusive system of FIG. 11 to practice the method of the invention.

Referring next to FIG. 12, the distal working end 540 is illustrate delivering energy to the volume of media 510 contained in the aneurysm sac 525. The delivering of energy is indicated by energy field EF that in this embodiment consists of electrical current between first polarity electrode 535 and a return electrode 565 that can be a ground pad as is known in the art. This step of the method causes resistive heating of the sacrificial shell portions 515 of the microspheres in a very brief time interval until the shells degrade to release their contents.

Figure 13:
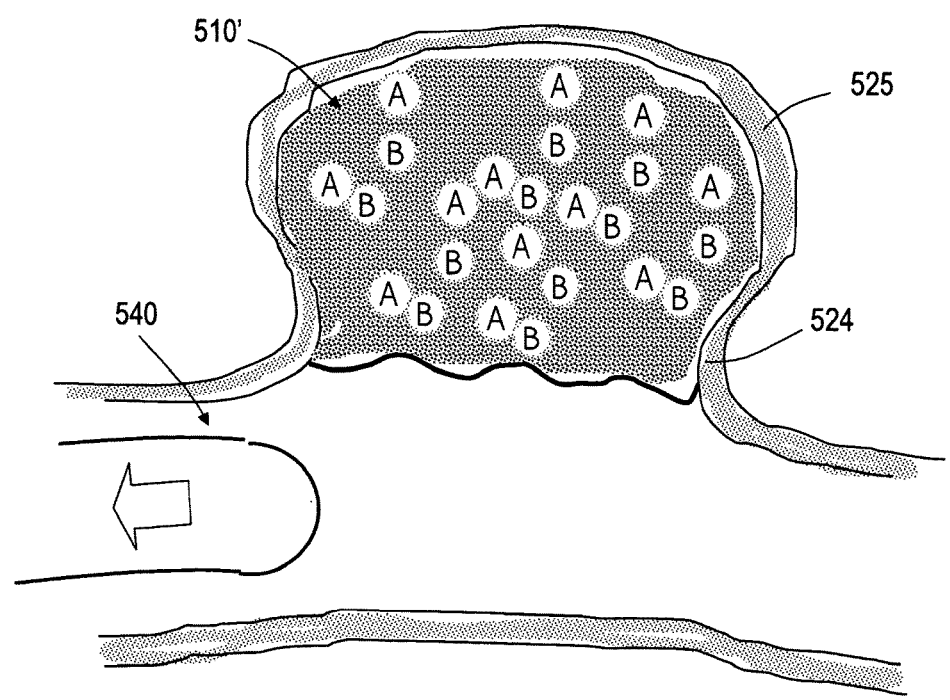
FIG. 13 is a view of a final step in practicing a method of the invention with the system of FIGS. 11-12.

FIG. 13 next schematically illustrates the interaction of the released cores 522 wherein the "A" and "B" compositions create a non-flowable volume of media 510' that occludes the aneurysm sac. FIG. 13 further illustrates the steps of collapsing the balloon member 556 and withdrawing the catheter from the targeted site.

In another embodiment (not shown), the catheter working end 540 can carry opposing polarity spaced apart first and second electrodes for delivering current to the conductive sacrificial shell portions 515 of the media in a bi-polar electrode arrangement in the working end.

In another embodiment (not shown), the energy emitter can be the terminal end of an optic fiber coupled to a light source, such as a laser. The sacrificial shell portions 515 of the media can carry any suitable chromophore for cooperating with a selected wavelength of the light source to again thermally degrade the sacrificial shell portions 515 of the microspheres. In all other respects, the system for occluding a vascular malformation is the same as described above.

5. Biomedical polymer composites. In another aspect, the invention comprises a new class of micro- or nanostructured polymer composites 600 that can be used for fuse-like embolic filaments as in FIG. 10. The new polymer composite 600 also can be used in several other biomedical applications, including forming the walls of hollow shells, spheres and the like. The invention comprises a polymer composite 600 of a micro- or nanostructured insulative filler material 610 dispersed within a base polymer 615 to form a matrix. In one embodiment of fuse-like or sacrificial polymer composite 600, the base polymer carries a conductive particle filler 618 dispersed within the matrix to provide a specified electrical resistivity as described in the earlier embodiments above. In general, the biomedical polymer composite has specified electrical resistance properties that allows it to perform in a fuse-like manner to melt, degrade or sacrifice in response to selected electrical parameters, such as voltage, current and duration of electrical energy delivery. For example, the sacrificial polymer composite can be used as a "fuse" to divide an embolic filament at the end of a catheter as in FIG. 7, or can be used to form the sacrificial walls of hollow spheres as in FIGS. 11-13. At the same time, the polymer composite 600 has unique thermal insulative properties and can be used to prevent propagation of thermal effects within the polymer or adjacent body structure.

Figure 14:
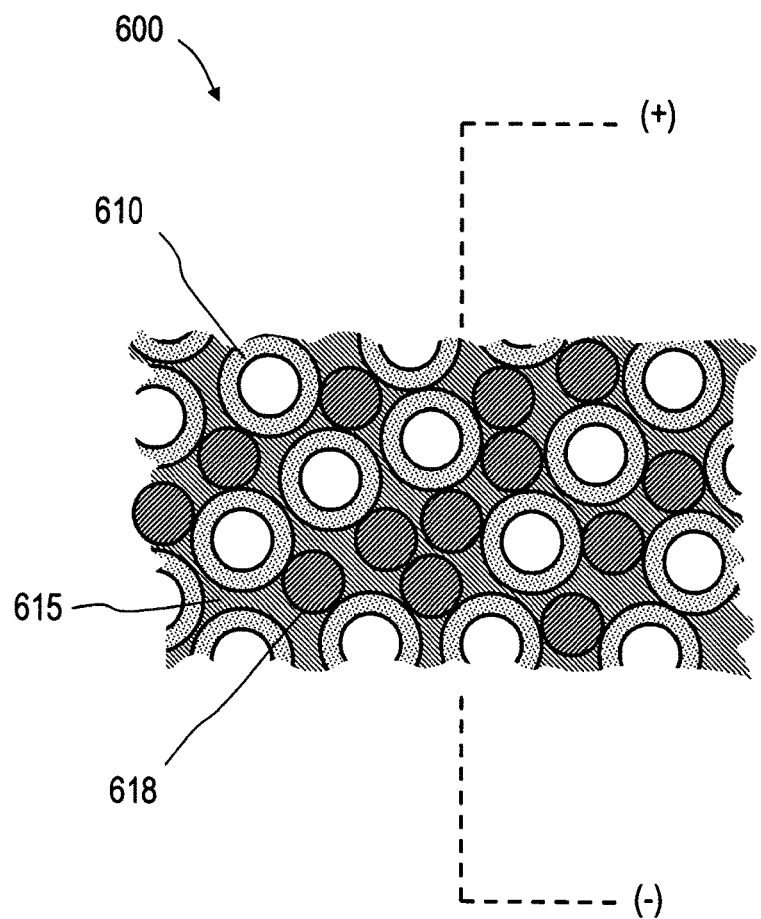
FIG. 14 is a schematic view of a polymer composite corresponding to the invention with a glass microsphere filler that exhibits an extraordinarily low thermal conductivity property.

The micro- or nanostructured insulative filler 610, in a preferred embodiment depicted in FIG. 14, comprises hollow microspheres that have extraordinarily low thermal conductivity properties. In one example, the filler material 610 consists of micron-dimension or nanoscale microspheres that are fabricated of a glass. In one embodiment, the insulative filler material comprises Q-CEL® hollow microspheres manufactured by Potters Industries, Inc., 820 Lufkin Road Apex, N.C. 27502-0298. The desired low thermal conductivity properties are provided by a glass material in the form of soda-lime glass or borosilicate. In another embodiment, the filler 610 can be hollow microspheres of Pyrex or any ceramic with a suitable low thermal conductivity. Thermal conductivity is a measure of the ability of a material of body to conduct heat, determined by the rate of heat flow normally through an area in the material divided by the area and by minus the component of the temperature gradient in the direction of flow, measured in W/m-K (watts per meter per degree Kelvin). In one embodiment, the filler material defines a thermal conductivity of less than about 5 W/m-K. Preferably, the insulative filler material 610 defines a thermal conductivity of less than about 2 W/m-K. More preferably, the insulative filler material 610 defines a thermal conductivity of less than about 0.5 W/m-K.

Referring to schematic view of FIG. 14, the base polymer 615 can be any biocompatible crystalline or semi-crystalline polymer. For example, the base polymer 615 can be at least one of the following materials: a polyamide, a polycarbonate, a polystyrene, a polyacrylonitrile, a polyacetal, a thermoplastic modified cellulose, a polysulfone, a thermoplastic polyester such as PET, poly(ethyl acrylate), or poly(methyl methacrylate), a nylon, a fluoropolymer such as polyvinylidene fluoride, an ethylene tetrafluoroethylene, or blends of two or more of the above polymers. The polymers described above are well known and are available from Dow Chemical, Union Carbide or Dupont-Mitsui Polychemicals Co., Ltd., all of which manufacture one or more of the above polymers. For embolic filaments and sacrificial hollow bodies, the insulative polymer composite 600 can provide much higher sensitivity to applied electrical energy to thereby melt or sacrifice instantly, while at the same time preventing thermal spread away from the targeted region of the polymer composite. The conductive filler material 618 can be any suitable biocompatible material, for example at least one of copper, aluminum, gold, iron, magnesium, molybdenum, nickel, palladium, platinum, silver, tantalum, tin, titanium, tungsten, zinc, or zirconium.

Figure 15A:
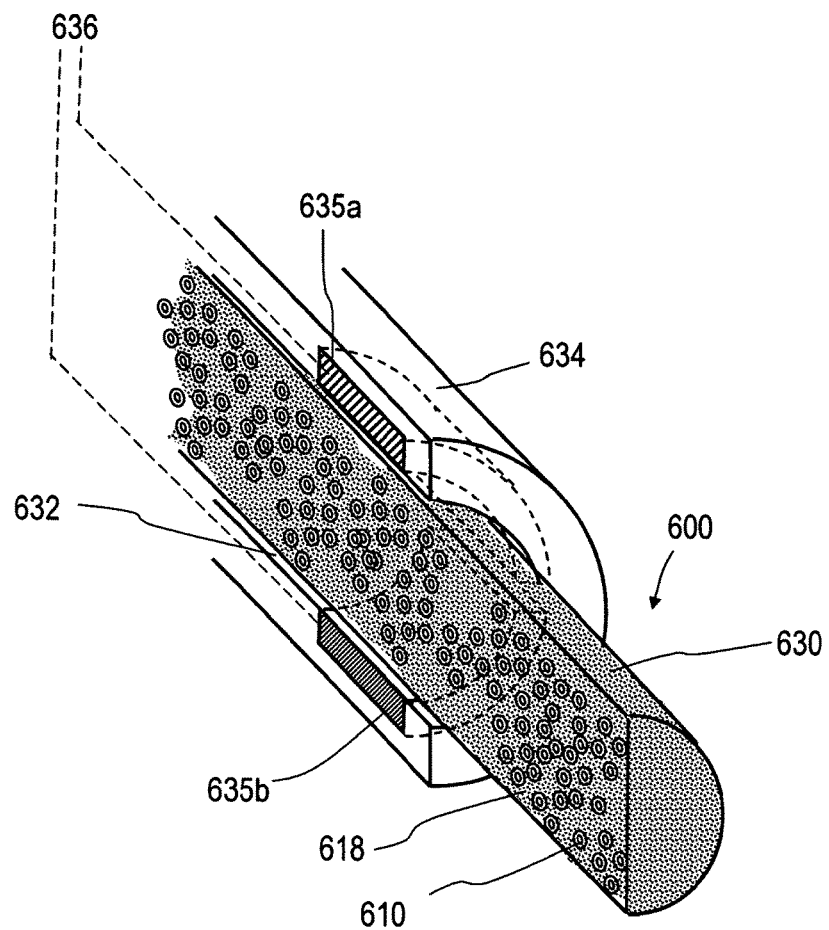
FIG. 15A illustrates a polymer composite embolic filament that carries glass microspheres with low thermal conductivity properties.
Figure 15B:
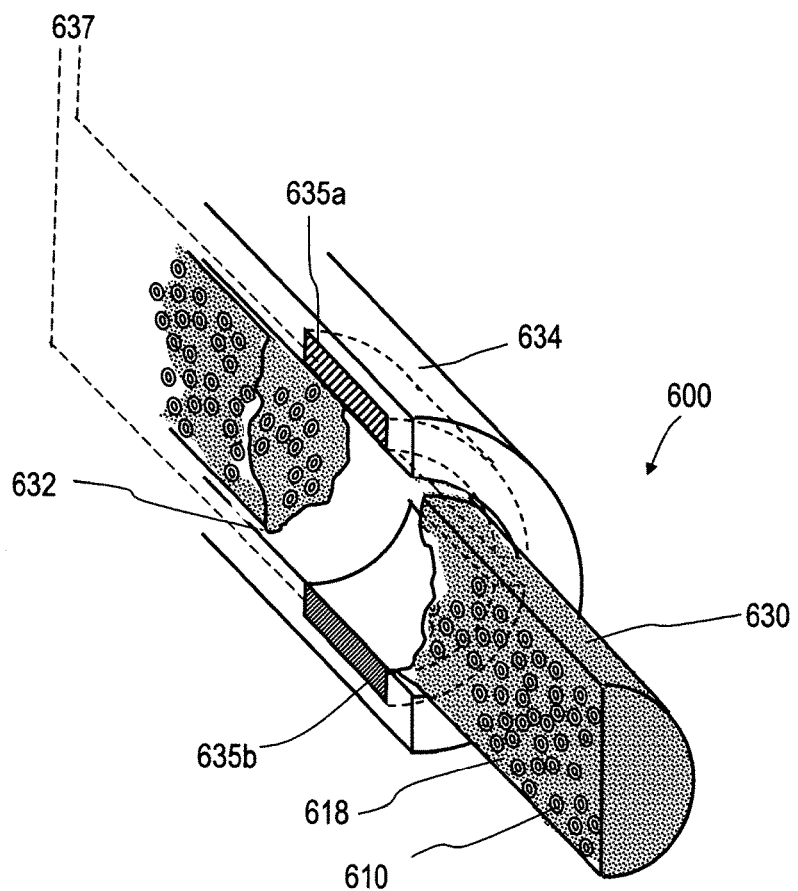
FIG. 15B illustrates the polymer composite filament of FIG. 15A in use with a catheter that applies energy between bi-polar electrodes to cause a fuse-like effect to divide the filament.

Referring to FIG. 15A, the advantages of the sacrificial polymer composite 600 can be understood in the context of a sacrificial embolic filament 630 for filing aneurysms, similar to that illustrated in FIG. 7 above. In the embodiment of FIG. 15A, the filament 630 entirely comprises the polymer composite 600 as described above with insulative filler microspheres 610 dispersed therein (not-to-scale). The filler material 610 preferably makes up more than about 5% by volume of the final polymeric composite 600. The filler material can comprise as much as about 80% by volume of the final polymeric composite 600. The polymer of the filament also is doped with electrically conductive particles 618 or microfilaments, such as carbon to provide the specified resistivity. The filament 630 has a stiffness akin to a monofilament fishing line that is suitable for pushing through channel 632 in catheter 634 from the handle end of the catheter. As can be seen in FIG. 15B, the catheter working end has opposing bi-polar electrodes 635a and 635b that are coupled to an electrical source 636 for applying energy to thermally melt and divide the filament 630. In use, the insulative microsphere filler 610 allows the filament to melt more rapidly since the melt volume is less due to the percentage volume of the microsphere filler 610. More important, the insulative microsphere filler 610 prevents the transfer of heat about the filament and into blood or adjacent body structure. Thus, the fuse-like process of dividing the filament 630 requires only instantaneous application of energy which will cause no collateral thermal effects damage.

Figure 15C:
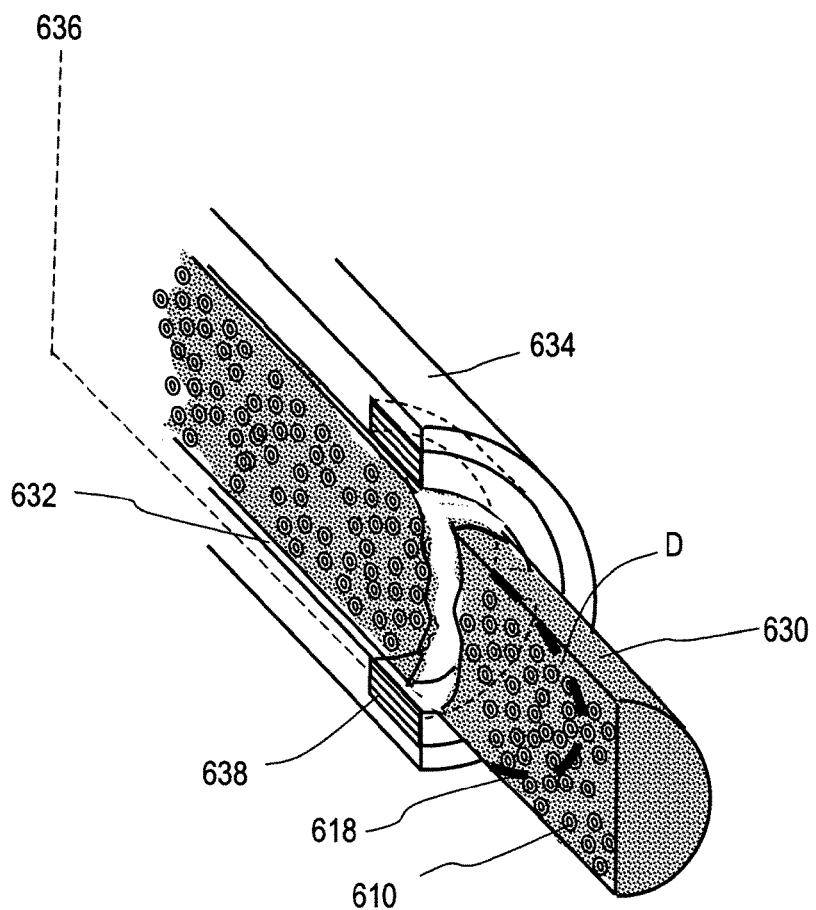
FIG. 15C illustrates a polymer composite filament as in FIGS. 15A-15B in a method of use wherein an alternative mono-polar electrode causes a fuse-like effect to divide the filament.

In FIG. 15C, a polymer composite filament 630 is shown in use with a catheter working end 634 that utilizes a mono-polar ring electrode 638 to melt and divide the filament. The ring electrode 638 extends 360.degree. about the end of the catheter and cooperates with a return ground pad 639 as is known in the art. As depicted in FIG. 15C, the filament 630 can be divided and melted across a very narrow cross-section of the filament wherein Rf energy density is localized at the end of the catheter. The heat effect caused within the filament 630 is prevented from propagating axially along the filament because of the insulative filler 610 within the polymer. In a filament 630 without an insulative filler 610, the filament would melt and divide across a broader cross-sectional region indicated at D in FIG. 15C. Thus, the insulative filler 610 has the effect of confining Rf energy density to a surface of the polymer or a plane proximate to the active electrode.

In another embodiment, the insulative filler material 610 consists of hollow micro- or nanospheres or tubes that also carry a selected gas within the hollow body. An inert gas (e.g., argon) would be useful in preventing or limiting oxidation in the composition during mixing and thereafter. The hollow micro- or nanospheres also can have a partial vacuum therein and can be compounded with the base polymer in a partial vacuum which can enhance the thermally non-conductive properties of the final polymer composite.

Figure 16:
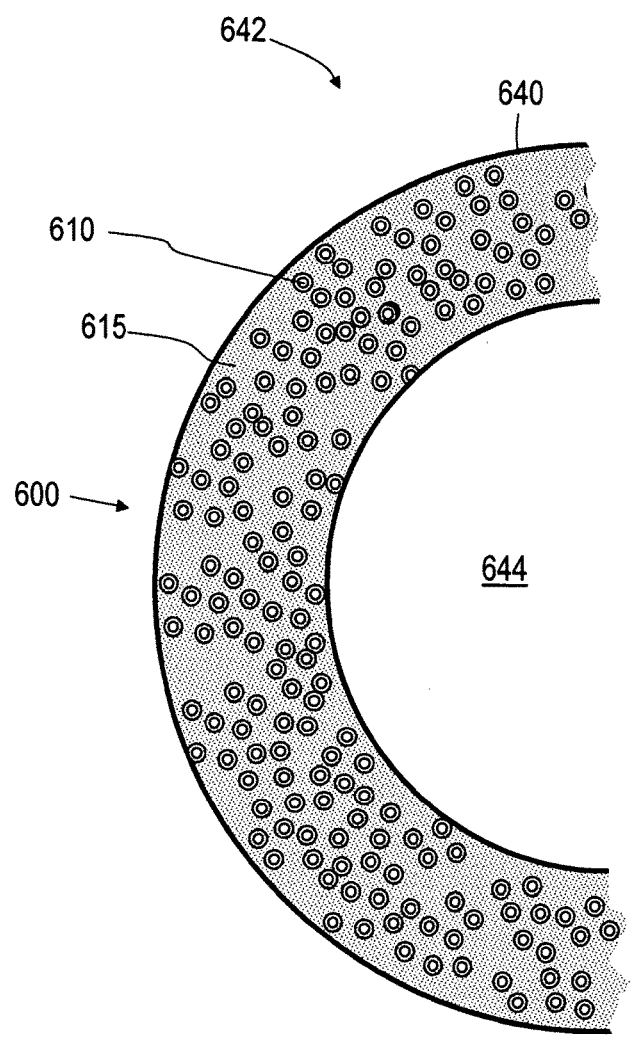
FIG. 16 is a schematic view of the polymer composite with an insulative filler formed into the sacrificial walls of a microsphere.
Figure 17:
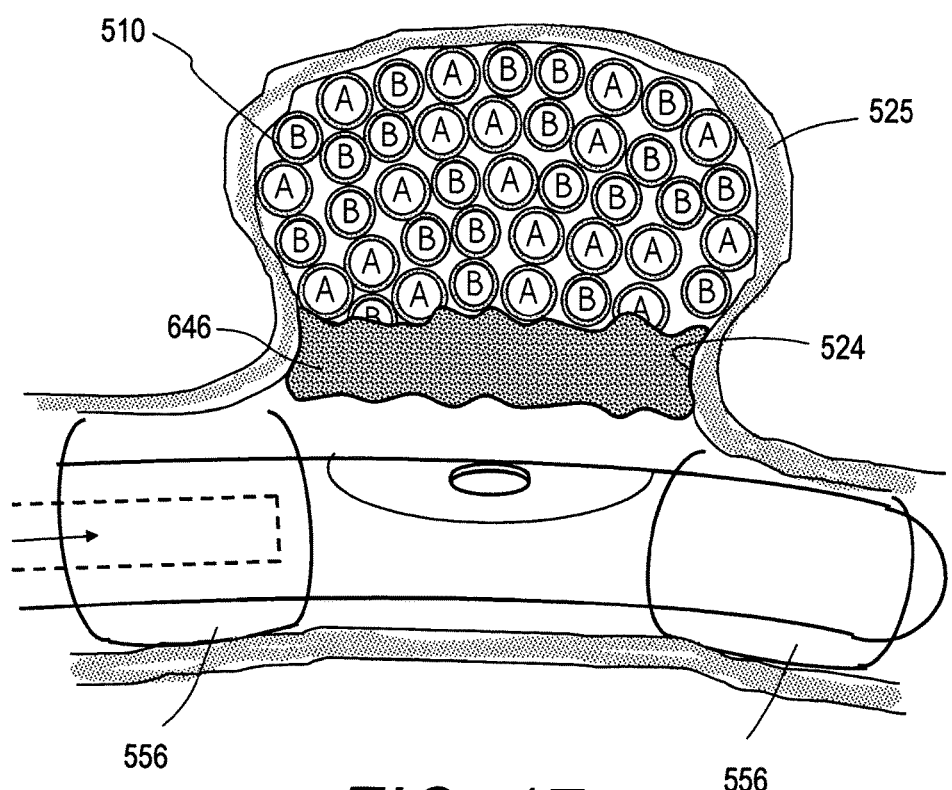
FIG. 17 is a schematic view of a polymer composite with an insulative filler used in a vaso-occlusive application.

In another embodiment shown schematically in FIG. 16, a polymer composite 600 similar to that described above is used to fabricate the walls 640 of any suitably dimensioned hollow sphere or tubule 642. The polymer wall 640 again carries an insulative filler material 610 having a thermal conductivity of less than about 5 W/m-K. Preferably, the insulative filler material 610 has a thermal conductivity of less than about 2 W/m-K, and more preferably less than about 0.5 W/m-K. In this embodiment, the filler material 610 also can be in the form of particles rather than hollow spheres, since the walls of a hollow shell may be very thin. The polymer again carries conductive filler particles 618 to provide a specified resistivity. The cores 644 of such hollow bodies carry the binary media as in FIGS. 11-13 that when released from the shells 642 can intermix and thereby change from a first flowable state to a second more solidified state. The improvement relates to the instantly thermally sacrificial properties of the polymer composite, which is similar to the sacrificial melting of the filament of FIG. 7. FIG. 17 is a schematic illustration of the use of such sacrificial walls 640 of microspheres wherein thermal propagation would be limited, which could in turn cause only the polymerization of a cap portion 646 of the implanted material.

In another embodiment, the sacrificial walls 640 are provided with hollow microspheres that also carry any drug. The sacrificial walls 640 can be melted or sacrificed by any thermal means, such as electric current delivered to conductively doped polymer composite walls having a specified resistivity, or inductive heating of ferromagnetic doped polymer composites, or light energy heating of a chromophore doped polymer composite.

Figure 18A:
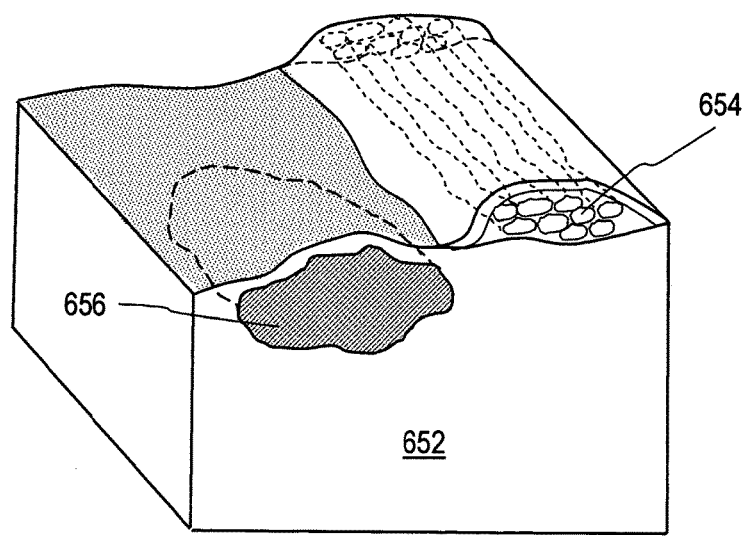
FIG. 18A is a schematic view of a tissue volume with a tumor targeted for thermal treatment and an adjacent nerve bundle.
Figure 18B:
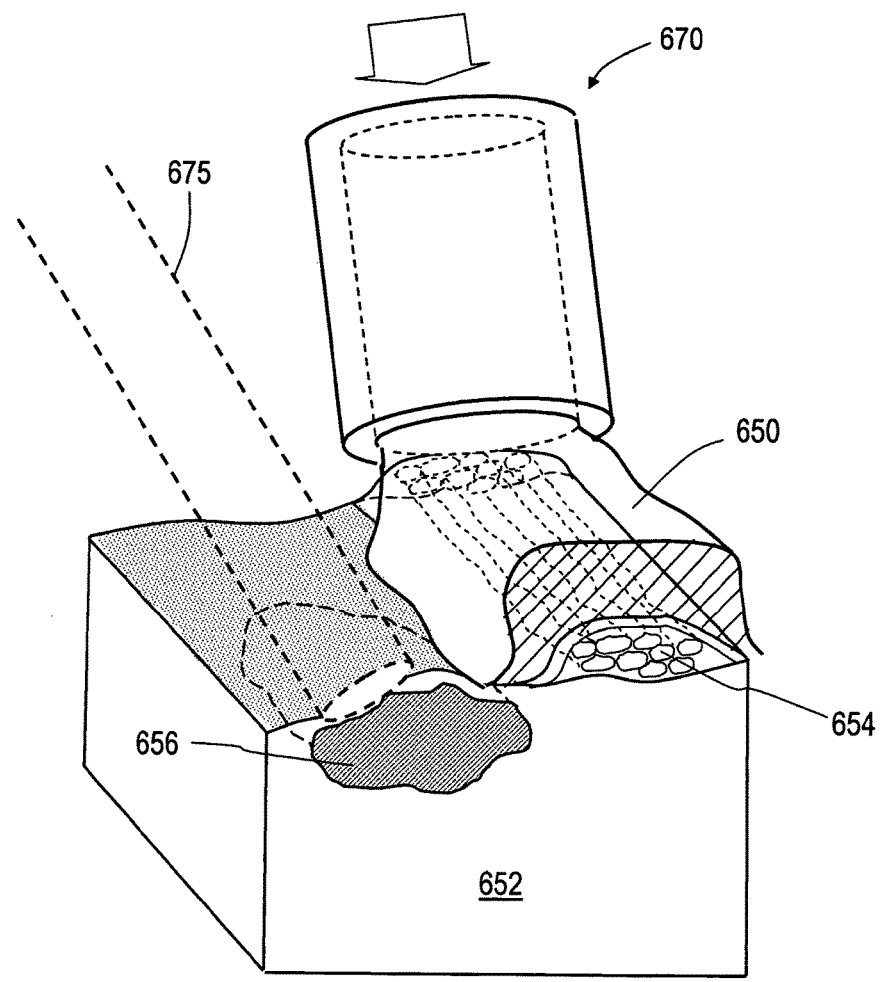
FIG. 18B is a schematic view of the tissue volume of FIG. 18A wherein a polymer composite with an insulative filler is used to protect the nerve bundle.

In another aspect of the invention, illustrated schematically in FIGS. 18A-18B, the insulative polymer composite or gel 650 can be used not to resistively heat and sacrifice the composite structure, but rather to thermally protect a targeted site against thermal effects while performing a thermally-mediated therapy on adjacent tissue. Such a thermally protective polymer composite 650 would be particularly useful, for example, in spine surgeries or neurosurgery applications wherein nerves must be protected from thermal damage. In the cartoon of FIG. 18A, a body structure 652 is shown that has a nerve bundle 654 in close proximity to a tumor 656 that is targeted for thermal ablation by laser or Rf energy delivery. FIG. 18B next illustrates the physician utilizing an introducer device 670 to introduce the polymer gel to cover the nerve bundle 654. The polymer composite or gel 650 can be any biocompatible or bio-absorbable base polymer 615 that preferably carries ultra-low thermally conductive nano- or microsphere filler 610 as described above. The filler material 610 can make up more from about 5% to 95% by volume of the final polymeric composite or gel 650. In this embodiment, the polymeric composite or gel 650 obviously does not carry a conductive filler component. As can be seen in FIG. 18B, an instrument such as a laser or Rf device 675 is indicated in phantom view in position to thermally ablate the tumor with nerve bundle 654 thermally protected by gel 650.

The polymer composites above are fabricated by mixing a precursor of the matrix material, i.e., the base polymer 615, with the non-conductive filler 610 and then processing the compositions to form the desired matrix material. The filler material or materials are mixed into the melt-state base polymer 615 until the filler materials are well dispersed. By any technique known in the art, the mixing is accomplished in a system that provides a temperature higher than the melting point of the polymeric base 615. In mixing the polymer base 615 with the insulative microspheres 610, together with the optional additives described below, the objective of mixing is to create a uniform dispersal of the filler material. In one method of fabricating the polymer composite 600 or 650, it has been found that an important step is providing an inert gas atmosphere (e.g., argon gas) in which the polymer is mixed at a selected temperature ranging between about 125.degree. C. and 300.degree. C. The protective gas atmosphere substantially eliminates oxidation that otherwise would occur to some extent within the base polymer. A particular advantage is that the mixing or compounding step can be extended in duration—even to one or more hours of mixing—without oxidation and degradation of the composite to allow uniform dispersal of the filler.

Other fillers can be included in the polymer composite 600 or 650, such as particles of magnesium or titanium, which are reductive and can assist in preventing oxidation within the polymer chains of the base polymer 615. The thermoplastic polymer base 615 can carry other additives known in the art, such as anti-arcing compositions, anti-oxidizing agents (magnesium oxide or titanium oxide), anti-ozonizing agents, cross-linking agents or any combination thereof. In the fabrication process, the mixture can also be treated with various cross-linking processes, both chemical and radiation (e.g., gamma, UV, E-beam irradiation), to cross-link the polymer or co-polymers of the matrix. In another embodiment, the hollow microspheres can carry any low thermal conductivity gas in the hollow core. For example, the microsphere cores can carry an anti-oxidant gas (e.g., $H_2$) or a gas that serves as a foaming agent. Alternatively, the hollow cores can be a partial vacuum. All these variations can add to the utility of the invention.

In another embodiment (not shown), the polymer composite or gel 650 as in FIG. 18A can carry a reversible thermochromic material that changes in color in response to thermal effects. A thermochromic agent or polymer can be incorporated into the base polymer during mixing. Articles containing 0.1% to about 2.0% by weight of thermochromic pigments in the host polymer can be designed to have a visually observable, reversible thermochromic transitions. Thermochromic materials are available from Chemsong, Inc., 923 Hawthorne Lane, West Chicago, Ill. 60185. It can be easily understood that the thermochromic effect, as in FIG. 18B, would allow the physician to easily guard against tissue overheating by simple observation of the thermochromic gel.

In another embodiment, the polymer can carry light-reflecting filler particles for reflecting light energy of selected wavelengths. Thus, the nerve bundle of FIG. 18B can be protected when light energy is used to thermally treat adjacent tissue.

Figure 19:
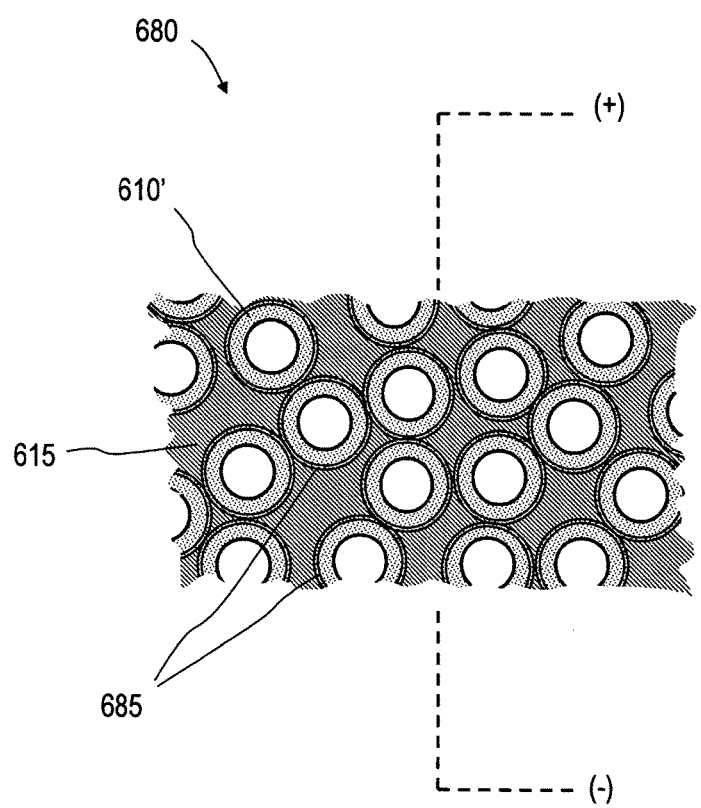
FIG. 19 is a schematic view of a polymer composite that carries glass microspheres with extraordinarily low thermal conductivity properties, wherein the microspheres have a metallic cladding.

In another embodiment depicted in FIG. 19, the polymer composition 680 has a base polymer 615 with an insulative component 610' of a different type. The insulative filler 610' again can be nano- or microspheres that have the same thermal conductivity properties as described above. In this embodiment, the insulative filler materials have a thin metal coating or cladding 685, for example a nanometric layer of gold, silver, platinum or another suitable metallic material that can be deposited by electroless plating or other means. In one embodiment, the metal coating is of a ferromagnetic material that will thus respond to inductive heating from an electromagnetic source. In this polymer composite, the single filler material functions as both the insulative component and the electrically conductive component to provide the specified resistivity. In another embodiment, the polymer composite can be used in any medical device, catheter or the like wherein the metallic coating provides radiopacity. In another embodiment, the base polymer 615 carries insulative hollow particles as described above for use in medical instruments to provide a polymer that responds optimally to ultrasound imaging.

FIGS. 20 through 22B illustrate an alternative embodiment of the invention wherein the polymer composite similar to that described above is used as a vaso-occlusive system 690. The system includes a catheter 692 with working end 695 that can introduce any selected length of a polymer composite 700 into an aneurysm. The polymer composite 700 this time comprises a flowable media within a catheter channel rather than being a solid filament. The polymer composite 700 again consists of a substantial volume of an insulative filler 710 in a base polymer 715 together with a conductive filler component 718, as described previously. More in particular, referring to FIG. 20, an elongate catheter 692 as is known in the art has a working end 695 with a central channel 722 extending along the catheter's axis 725. The catheter diameter and the thickness of the wall 726 that surrounds the central channel 722 can be any suitable dimension to provide suitable flexibility and pushability for navigating to a targeted endovascular location.

Figure 20:
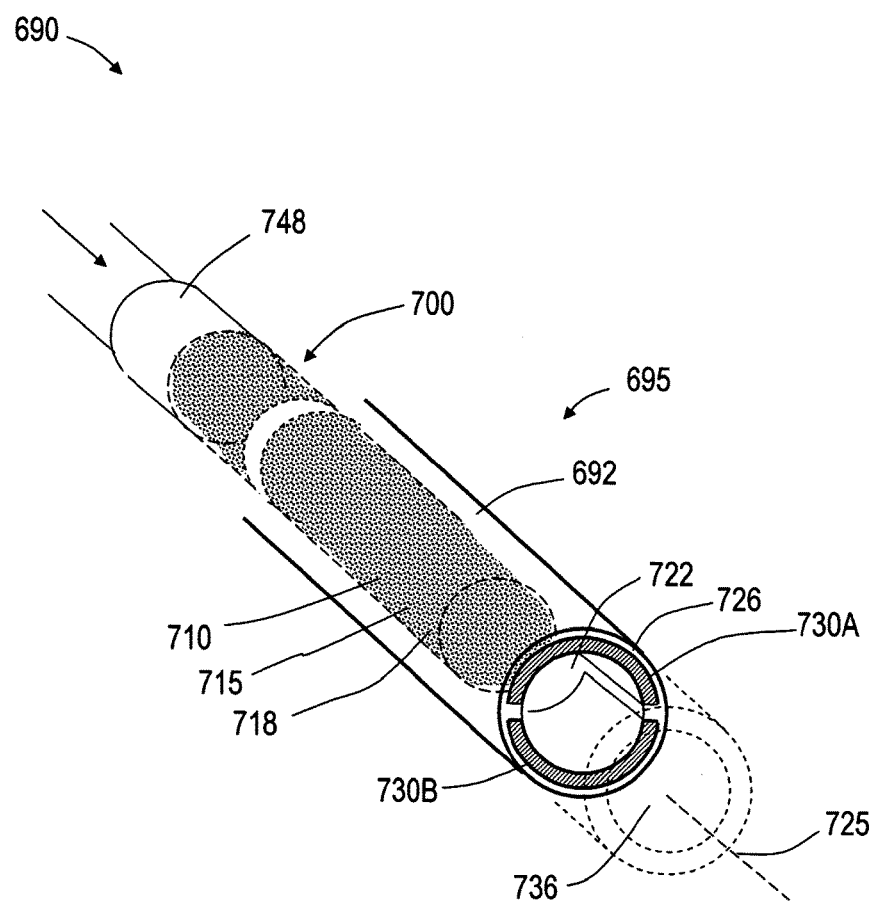
FIG. 20 is a schematic view of an alternative vaso-occlusive system that provides a thermoset polymer gel within the catheter that is extrudable from the catheter working end.
Figure 21:
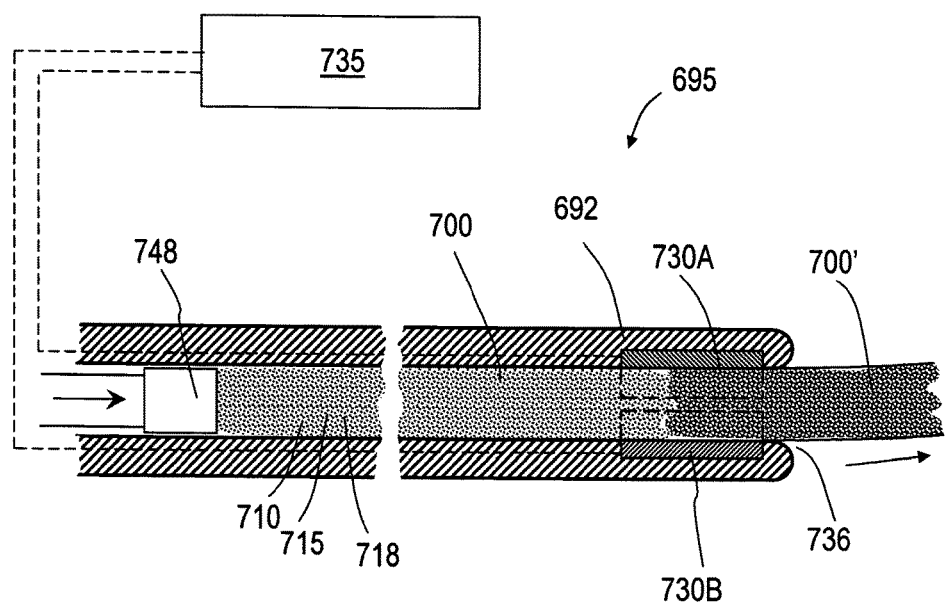
FIG. 21 is a sectional view of the vaso-occlusive system of FIG. 20 illustrating the gel-like polymer being altered from a first flowable state to a second non-flowable filament state.

The sectional view of FIG. 21 shows that the channel 722 of catheter working end 695 carries first and second spaced apart electrodes 730A and 730B that have opposing polarities as defined by the electrical source 735 coupled to the electrodes. In the exemplary embodiment of FIGS. 20 and 21, the electrodes 730A and 730B are shown as being positioned on opposing sides of the channel 722 but the electrodes also can be ring-type electrodes space apart axially close to the open termination 736 of the channel. Preferably, the exposed surfaces of the electrodes 730A and 730B are spaced inward from the open channel termination 736.

Still referring to FIG. 20, an elongate portion of channel 722 carries a fluid or gel-like composite 700 wherein the base polymer 715 comprise a biocompatible thermoset type of polymer. The composite 700 carries any suitable conductive or "radiosensitive" compositions 718, which provide the thermoset base polymer 715 with the specified resistivity that cooperates with the electrodes 730A and 730B to elevate the temperature of the composite 700 when "engaged" by the electrode arrangement. In one embodiment, the radiosensitive filler composition 718 comprises electrically conductive carbon particles ranging from about 10 nm to 100 microns in cross section. The conductive filler alternatively can be any other conductive particle or microfilament of gold, silver or the like. Also, the composite 700 carries a radio-opaque composition (not shown) that cooperates with a selected imaging system to allow imaging of the introduction of the composite into an aneurysm.

FIGS. 20 and 21 illustrate that the gel-like composite 700 can extend through a very elongate section of channel 722 to carry a sufficient volume of media to fill a targeted aneurysm. The flowable composite 700 can be pushed outward of the distal termination of channel 722 by a pusher rod mechanism indicated at 748. The distal end of the pusher 748 is in contact with the gel-like composite 700 and the proximal end of the pusher extends outwardly of the handle portion (not shown) of the catheter for manipulation and advancement by the physician. In FIG. 21, it can be seen that contemporaneous pushing of composite 700 through the region of its engagement by energized electrodes 730A and 730B will cause its elevation in temperature and conversion to thermoset solid polymer 700'. This solid filament-like media 700' can be extended or extruded in any selected length in the aneurysm (FIG. 22A).

It should be appreciated that the media 700' can be extended outwardly from the distal tip of the catheter or from a side port in the side wall of the catheter working end. Further, the working end can carry one of more balloons or other expansion structures for stabilizing the catheter working end proximate to the neck of an aneurysm. Still further, the catheter working end can carry a plurality of opening through which the media 700' can be pushed with each such opening having a cooperating electrode arrangement.

Figure 22A:
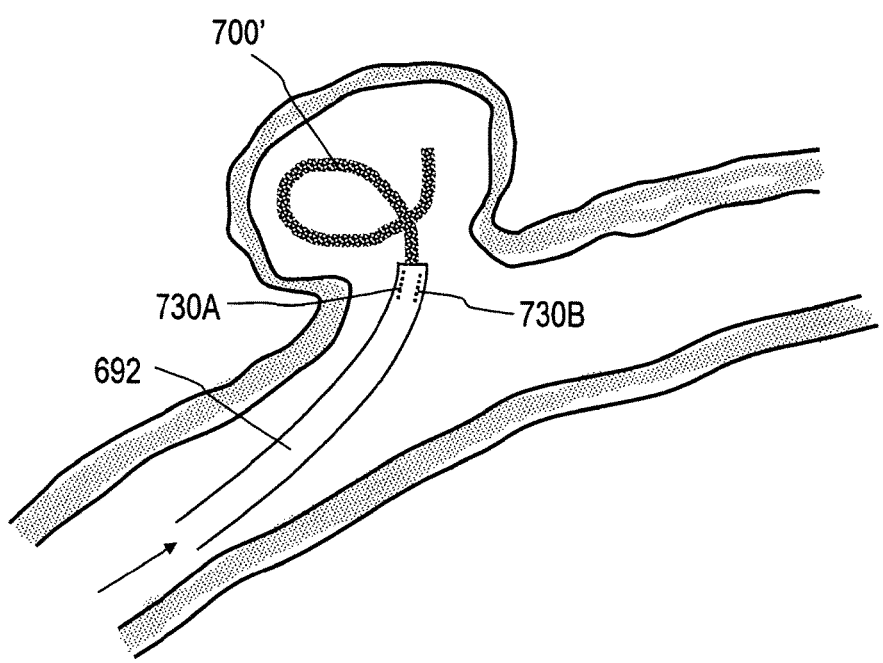
FIG. 22A illustrates a first step in the method of use of the vaso-occlusive system of FIGS. 20-21.
Figure 22B:
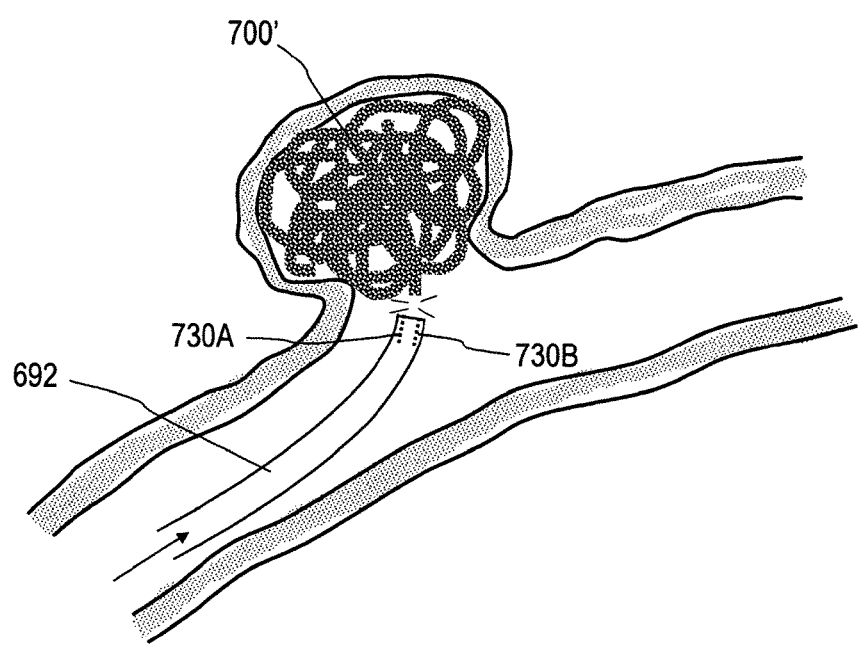
FIG. 22B illustrates another step in the method of using the vaso-occlusive system of FIG. 22A.

Now turning to FIGS. 22A-22B, the method of practicing the invention utilizing the system of FIG. 20 is illustrated. In FIG. 22A, the working end of catheter 692 is shown as being introduced endovascularly to the neck of an aneurysm. In FIG. 22B, the physician then activates the energy source while contemporaneously advancing the pusher 748 to extend, extrude and alter the media into a thermoset filament media 700' that extends from the open catheter end into the aneurysm. In this first step of the method of the invention in one mode of operation, a computer controller coupled to the electrical source can be coupled to a pressure sensor or flow sensor in the working end of the catheter 692 to modulate energy delivery between selected power levels depending on the rate of flow of media across the interface with the electrodes. In another mode of operation, the catheter working end can carry multiple pairs of electrodes and deliver a different selected level of power to each electrode pair. By this means, stresses can be induced into the thermoset filament 710' resulting in the filament assuming a curved shape after exiting the catheter. The multiple paired electrodes also can be carried at various different depths within the channel 722 to induce stresses in the extruded filament media 700' to produce a curvilinear, twisted or helical filament shape, of any combination thereof. It is believed that such a curvilinear filament will be more easily packed into an aneurysm.

As can seen in FIG. 22B, at least one selected length of a solid filament media 700' has been introduced into aneurysm to substantially occlude the malformation. Another optional step and mode of operation of the invention can be understood from FIG. 22B, which is similar to that described in the Types "A" and "C" embodiments and FIG. 6C above. This method relates to a controlled method of energy delivery to the extended filament media 700' within the aneurysm in a self-limiting process to cause coagulative material to form around the filament to further occlude the aneurysm. This aspect of the method comprises the steps of (a) providing the filament conductive polymer composite that defines a positive temperature coefficient (PTC) of resistance; (b) engaging body media such a blood with the polymer composite; (c) applying electrical energy via electrodes to the polymer composite; and (d) self-limiting the application of Rf energy to the body media as a result of the PTC effect in the polymer composite. In other words, at any time that a selected portion of the filament is elevated over a switching temperature of the PTC as it senses and responds to adjacent ohmically heated body media, that portion of the filament becomes substantially resistive and terminates current flow therethrough. To accomplish this method of the invention, the controller would typically define both electrodes 730A and 730B of the catheter with a first polarity that would cooperate with a return electrode comprising a ground pad (not shown). In this aspect of the method, another selected power level would be provided to accomplish the energy delivery to the blood.

FIG. 22B further illustrates the final step of the method of the invention, as in FIG. 7B, wherein the system detaches the extruded filament media 700' from the catheter and the gel composite 700 that is still carried within the catheter lumen 722. In one method, the gel composite 700 is sufficiently soft so that the extruded portion naturally decouples from the gel at the interface between the non-thermoset portion 700 and the thermoset portion 700'. In another embodiment, as when the gel composite 700 is stiff or the media carries conductive microfilaments, the detachment can be accomplished as described previously with a very brief application of higher level of energy to melt the filament wherein it functions as a fuse.

Figure 23:
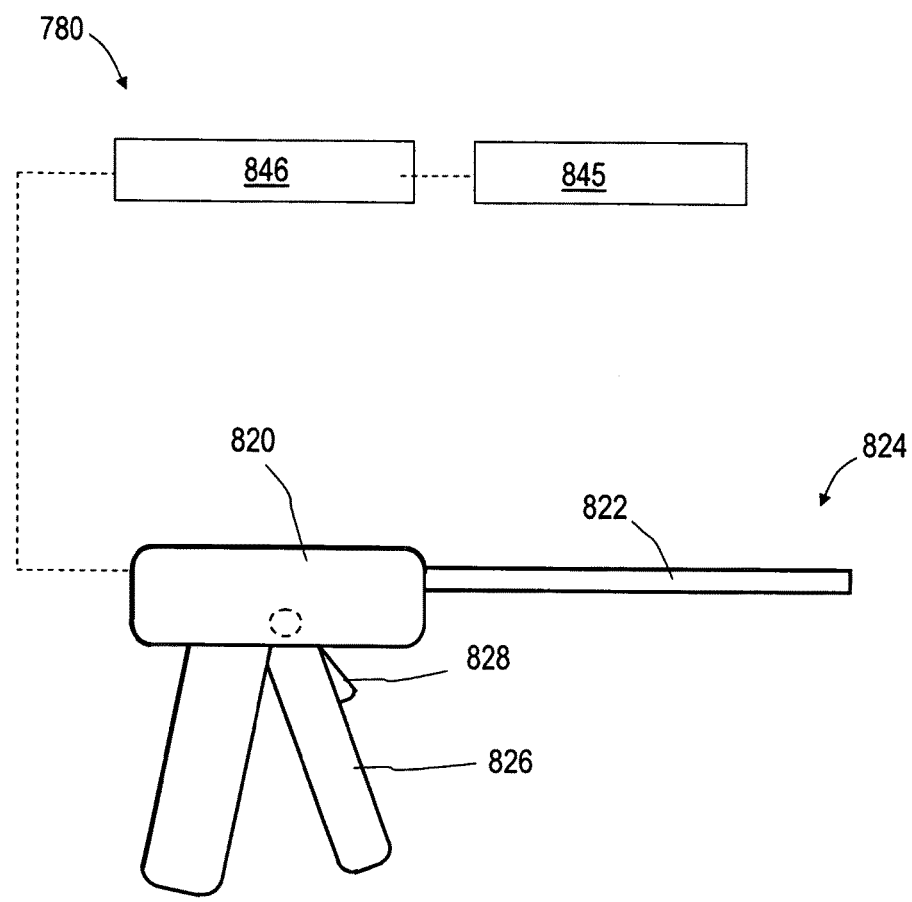
FIG. 23 shows a plan view of an exemplary hand-held instrument with a working end that extrudes bi-polar conforming gel ribbons.
Figure 24:
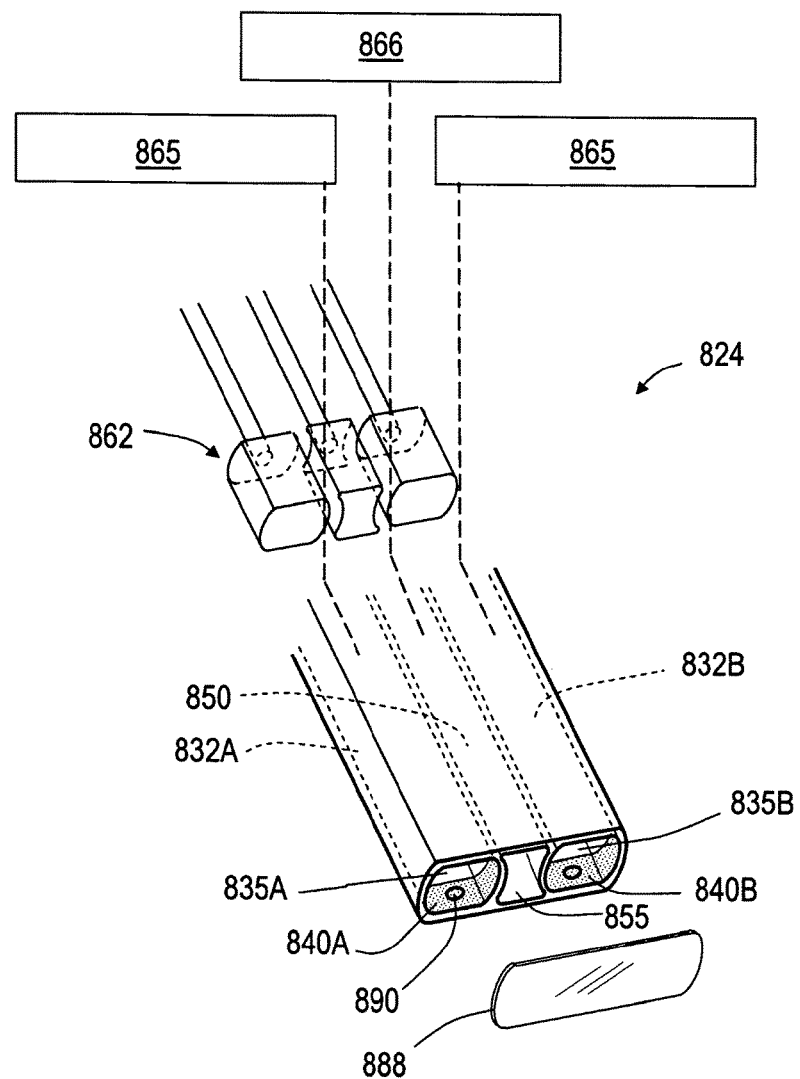
FIG. 24 is an enlarged cut-away view of the working end of the instrument of FIG. 23 showing spaced apart channels for extruding paired conductive gel ribbons together with an intermediate non-conductive gel ribbon.
Figure 25:
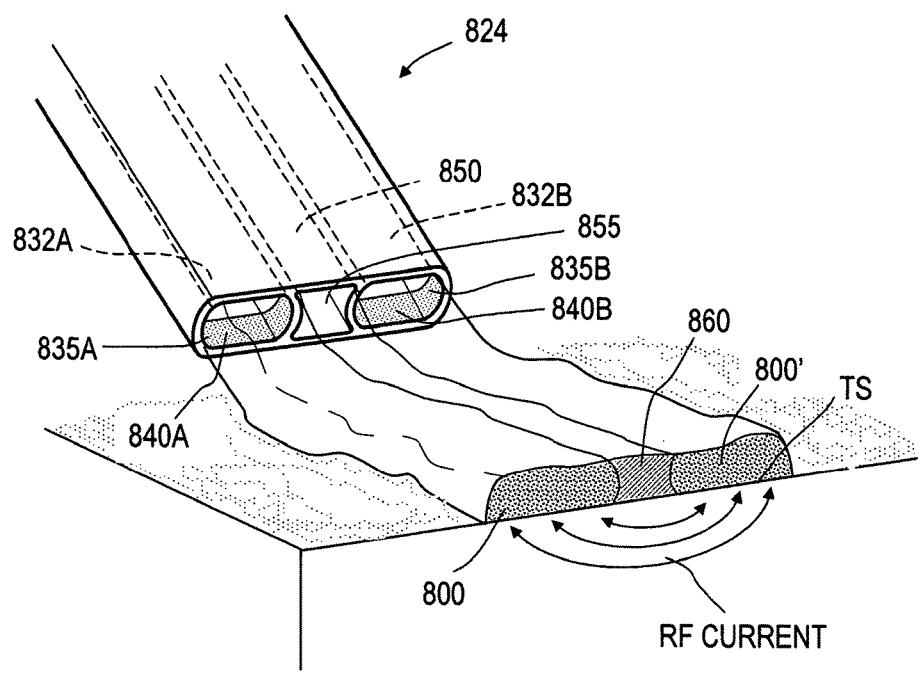
FIG. 25 is a graphic illustration of the manner of practicing a method of the invention in extruding a bi-polar gel electrode over a targeted site.

FIGS. 23-25 are views of an alternative instrument 780 for delivering energy to tissue surfaces that uses polymer composites 800 similar to that described above. Again, the polymer composite 800 consists of a substantial volume of an insulative filler 810 in a base polymer 815 together with a conductive filler component 818. In one embodiment of FIG. 23, the instrument has a proximal handle 820 as is known the art with an elongate introducer portion 822 that extends to a working end 824. The introducer portion 822 can have any suitable cross-section and length for use in endoscopic or open surgeries. The handle 820 carries a pivotable actuating lever or slide actuator 826 for extruding the flowable composite 800 from the working end 824. The handle also carries a trigger indicated at 828 for actuating electrosurgical energy delivery to the working end and thereby to the polymer gel composite 700. The gel-extruding actuator 826 and electrosurgical trigger 828 optionally can be interlinked to work in unison.

FIG. 24 is a partially cut-away view of the working end 824 of instrument 780 for extruding and painting the flowable composite 800 across a targeted site on a body structure, wherein the composite can function as a bi-polar electrode arrangement. The working end 824 defines paired spaced apart (first and second) channels 832A and 832B that carry the flowable conductive polymer composite 800 that can have the consistency of a think paint or gel. It can be seen that each channel 832A and 832B terminates in a media outflow port or opening indicated at 835A and 835B, respectively. First and second electrodes 840A and 840B have exposed surfaces that extend inwardly from the media outflow ports 835A and 835B. Each electrode 840A and 840B is coupled by an electrical lead to an electrosurgical generator 845 and 846 (see FIG. 23).

The working end 824 further defines an intermediate channel 850 that extends to a third media outflow port 855A that extrudes a flowable non-conductive polymer composition 860. The intermediate outflow port 855A is positioned between the paired outflow ports 835A and 835B that extrude the flowable conductive media 800. In one preferred embodiment, the conductive media 800 and the non-conductive media 860 are adapted with different colors (and/or transparency) to provide a visual indicator of the non-conductive media being properly extruded between the conductive gel ribbons. For example, the conductive gel ribbons can be a first color or be transparent or translucent, and the intermediate non-conductive gel can be a second contrasting color. Both the electrically conductive gel 800 and non-conductive gel preferably carry the insulative microsphere filler material 810 as described above, which will assist in preventing unwanted thermal effects in tissue that is not targeted for treatment.

In one exemplary embodiment shown in FIG. 24, the instrument provides means for simultaneously extruding ribbons of gel from the working end 824. In FIG. 24, the instrument has a set of cooperating axially-extending plungers indicated at 862. In this embodiment, the reservoir of conductive gel composite 800 and non-conductive gel composite 860 consist of the selected lengths of the gel in channels 832A, 832B and 850 within introducer member 822. The instrument carries mechanical linkage as is known in the art wherein the lever actuator 826 would ratchet to advance the set of plungers 862 distally to push the gel ribbons outwardly from the distal end.

In another embodiment (not shown) the channels 832A, 832B and 850 within the working end are in fluid communication with first and second gel reservoirs 865 and 866 (FIG. 24) that carry the conductive media 800 and non-conductive media 860, respectively. Such gel reservoirs (see FIG. 24) can be carried in the handle 820 of the instrument or be remote from the handle and communicate therewith through flexible tubing. In this embodiment, a back-and-forth stroke of the lever actuator 826 would pull volumes of gel media into channels 832A, 832B and 850, and then extrude the gel volumes from the working end. Any other pressurization systems or hydraulic system can be used to extrude that gels and fall within the scope of the invention.

Referring again to FIG. 24, it can be seen that the working end 824 is covered with a thin film seal indicated at 888 that can be removed just prior to use. Optionally, the seal 888 can be a burstable film element that bursts on the application of pressure when the gel begins to be extruded from the working end. It should be appreciated that the introducer member 822 (see FIG. 23) can be flexible, articulatable, deflectable or deformable and fall within the scope of the invention. For example, a flexible or articulatable gel bi-polar electrode extruding system can be developed for introduction through a working channel of an endoscope.

Now turning to FIG. 25, the method of the invention is illustrated wherein energy is applied to a treatment site TS in the form of controlled depth ohmic heating based on the center-to-center distance between the conductive gel ribbons. In FIG. 25, it can be seen that the two ribbons of conductive media 800 and 800' are extruded from the working end 824 at the same time as an intermediate ribbon of non-conductive media 860 is extruded. The gel extrusion process allows the physician to "paint" the working end 824 across a targeted treatment site TS. Contemporaneous with the extrusion of the gel ribbons, the physician actuates the trigger 828 to apply alternating Rf current to the opposing polarity electrodes 840A and 840B. The conductive gel ribbons 800 and 800' are in contact with the electrodes 840A and 840B at the same time that the gel conforms to, and flows over, the irregular surface of the anatomic structure. No matter how irregular the tissue surface, the Rf energy applied to the electrode ribbons will create a substantially uniform depth of ohmic heating of tissue, whether the objective is coagulation at lower temperatures, or a form of tissue ablation at higher temperatures. In FIG. 25, the arrows indicate the current flow within the tissue surface.

The type of energy delivery illustrated in FIG. 25 can be used in sealing the surface of an organ, such as a liver, kidney, pancreas or lung. In a similar method of use, an instrument can be dimensioned to apply bi-polar gel electrodes around the pulmonary vessels to create elongate lesions in the vessel wells for creating, or blocking, conduction pathways as is known in the art.

The system optionally provides feedback control mechanisms within controller 846 for modulating energy delivery to electrodes 840A and 840B and thereby to the conductive gel electrodes. Referring again to FIG. 25, at least one thermocouple 890 can be provided proximate to the electrodes to measure the temperature of each electrode which resembles the surface temperature of the targeted site. The thermocouple 890 is linked to controller 846 by an electrical lead (not shown). The controller 846 is provided with software and algorithms that are adapted to modulate power delivery from electrical source 845 to maintain the temperature of the electrodes at a particular level or within a particular temperature range, in response to feedback from the sensor.

In a preferred mode of operation, the thermocouple 890 (see FIG. 24) together with feedback circuitry to the controller 846 are used to modulate power delivery to the electrodes to maintain their temperature at a pre-selected temperature level for a selected period of time. The method of invention maintains the electrodes within a range of about 60.degree. C. to 200.degree. C. More preferably, the surface temperature is maintained within a range of about 70.degree. C. to 100.degree. C.

In another preferred embodiment, the conductive gel ribbons 800 and 800' can carry a biocompatible or bioresorbable thermochromic composition. Such a thermochromic material can be designed to change its color in response to temperature and thereby can provide the physician with an excellent visual indicator of the temperature of the gel, which reflects the temperature of the treated tissue. The phenomenon of thermochromism can be defined as the reversible change of a color of a material in response to change in temperature. As one example, the composition can exhibit a thermodynamic phase between the pure solid and pure liquid phases and be microencapsulated and carried in a polymer host that is dispersed in the gel. At any temperature below a selected "event" temperature, the thermochromic material can be designed to be a transparent or translucent solid. At a selected thermochromic transition temperature or event temperature, the material will reflect visible light of a unique wavelength to provide an indicator to the physician.

The temperature sensitive thermochromic material also can be adapted to reversibly change its color at any selected thermochromic transition temperature, for example a temperature between 50.degree. C. to 200.degree. C., depending on the application. More preferably, the thermochromic transition temperature is between 70.degree. C. to 100.degree. C. The thermochromic transition temperature is typically based on the structure of the polymer or oligomer-based pigment that can be adjusted by chemical modifications. The transition color can be any selected color, for example the thermochromic material can change from translucent to red at the selected thermochromic transition temperature. One source of thermochromic materials for including in the gel matrix of the invention is International Ink Co., 775 Dorsey Street, Gainesville Ga. 30501.

Figure 26:
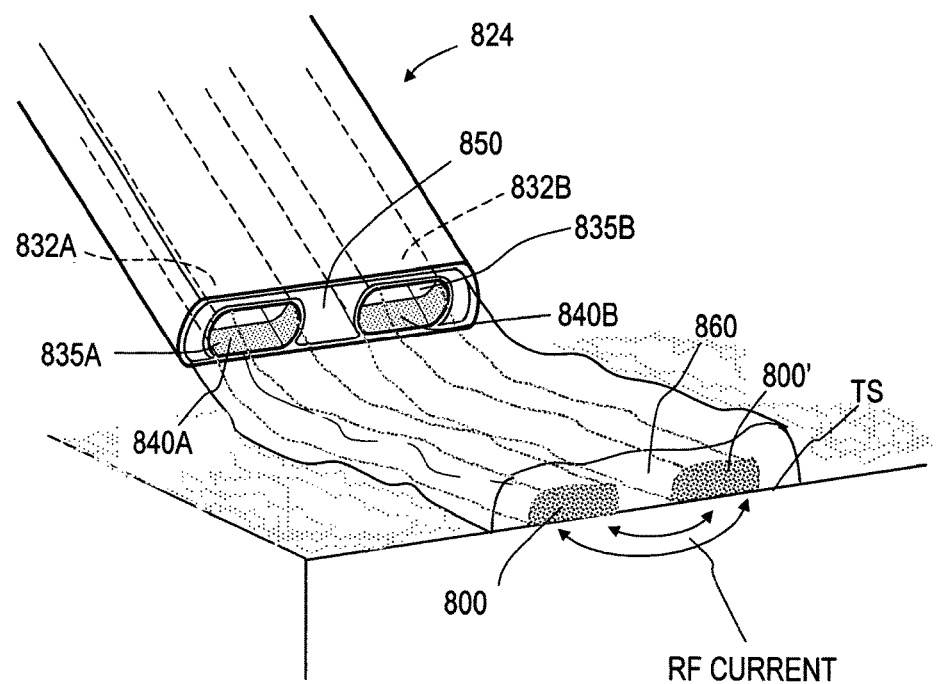
FIG. 26 illustrates an alternative embodiment of instrument and its method of use in extruding a bi-polar gel electrode over a targeted site.

Now turning to FIG. 26, an alternative working end 895 and its method of use are illustrated for applying a bi-polar composite gel electrode to a targeted site. In this embodiment, the two ribbons of conductive media 800 and 800' again are extruded from the working end 824. In this embodiment, the channel 850 that extrudes the intermediate ribbon of non-conductive media 860 is configured to extend between and over the exterior surfaces of the ribbons of conductive media 800 and 800'. The system and method illustrated in FIG. 26 would thus prevent electrosurgical energy delivery to non-targeted tissues that might fall into contact with the gel-electrode ribbons since the entire surface of the extruded gels is encapsulated with a layer of the non-conductive gel. Further, the gel strips could be painted over one another to provide a more complete coverage of a targeted site.

In any embodiment of conductive media 800, the scope of the invention includes any flowable media such as a gel, paste, liquid, colloid or suspension in which the matrix of the media comprises a biocompatible flowable material together with a biocompatible conductive composition therein. The invention further includes any gel, paste or liquid with a saline solution component that can provide a change in media conductivity as the media is dried by energy delivery therethrough. In one embodiment, the desiccation of a saline component can be designed to make greater contacts between the conductive microfibrils or compositions in the media to thereby increase its conductivity. In another embodiment, a highly conductive saline can be used wherein its desiccation can reduce contact between conductive particles to decrease its conductivity.

In any embodiment of conductive media 800, all materials and components of the media can be bioabsorbable. Further, the media can create a seal over the treatment area. Antibiotics and other pharmacologically active compositions can be provided in the media.

As described above, the hollow ceramic or glass nano- or microspheres when dispersed within a polymer, gel or fluid volumes (collectively imageable media) are well suited to allow ultrasound imaging of the volume after introduction into the interior of a patient's body. The nano- or microspheres also can be fabricated, at least in part, of a radiosensitive imaging material, or clad in such a radiosensitive material layer. For example, a gold layer can be provided on the nano- or microspheres to allow for x-ray and similar types of imaging. The scope of the system embodiments and methods corresponding to the invention encompasses the use of such imageable media for introduction into vascular malformations in the interior of the body for uses that benefit from ultrasound imageability. The scope of the invention includes the use of such imageable media for any therapeutic applications at any location in a patient's body.

In one example, biocompatible nano- or microspheres can be dispersed in any biocompatible fluid or gel-like media, including collagen filler media, for use as an imageable filler material for dermatology and reconstructive surgery applications. In one example, the inventive media can be used after tumor removal to replace the excised tissue volume. In breast lumpectomies, the filler material then would be imageable to ascertain treatment margins and allow a baseline 3D volume for later reference in follow-up exams. In this system embodiment, the media functions only in an imaging capacity.

In another embodiment, the imageable media can function in a linked manner to function both in an imaging function and in an energy application function. In one example, the inventive imageable filler material can be introduced into a patient's body as a dermatological filler, wherein the filler also carries an energy-responsive composition as described above (a magnetic responsive composition, a radiosensitive composition, or a chromophore) for cooperating with an external energy source. Such a filler can be used advantageously in a thermally mediated treatment to cause collagen shrinkage, to cause a wound-healing response for inducing collagen formation, or generally to cause thermal tissue stimulation. The method and system of the invention comprises (i) using the ultrasound imaging means to scan a selected area or volume of tissue; (ii) utilizing algorithms in an imaging controller system to determine the distribution of the media within the scanned area, or more particularly the distribution of the energy-responsive composition within the scanned area; and (iii) utilizing the data on media distribution to adjust energy levels and localization of energy delivery to cause a selected thermal effect within the tissue—no matter the lack of control over media migration in the tissue.

Those skilled in the art will appreciate that the exemplary embodiments and descriptions of the invention herein are merely illustrative of the invention as a whole. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only being the true purview, spirit and scope of the invention.

What is claimed is:

1. An apparatus for thermally treating tissue, comprising:
  an elongate introducer having a proximal end, a distal end, and an interior passageway extending from the proximal end to an opening in the distal end;
    a flowable insulative material carried in or otherwise in fluid communication with the interior passageway;
    at least one electrode coupled to or proximate to the distal end of the introducer;
    an energy delivery actuator configured to controllably energize the at least one electrode; and
    a flow actuator configured to actuate a controlled flow of the flowable insulative material from the interior passageway through the distal end opening and outwardly from the distal end of the introducer;
    wherein the flowable insulative material comprises a base polymer and dispersed nonconductive filler.

2. The apparatus of claim 1, wherein the flow actuator comprises a member configured for pushing the flowable insulative material through the interior passageway.

3. The apparatus of claim 1, wherein the energy delivery actuator comprises a switch.

4. The apparatus of claim 1, wherein the flow actuator and energy delivery actuator are operatively coupled with one another and configured to operate in unison.

5. The apparatus of claim 4, wherein the flow actuator and energy delivery actuator are operatively coupled to a same actuating switch mechanism.

6. The apparatus of claim 5, further comprising a handle coupled to the proximal end of the elongate introducer, wherein the actuating switch mechanism comprising a trigger coupled to the handle.

7. A system for thermally treating tissue, the system including the apparatus of claim 1, and further comprising a respective power generator and controller operatively coupled to the at least one electrode.

8. The system of claim 1, wherein the nonconductive filler comprises hollow microspheres.

9. The system of claim 1, wherein the base polymer and nonconductive filler comprise bio-absorbable materials.

10. The system of claim 1, wherein the base polymer is selected from the group consisting of: polyamide, polycarbonate, polystyrene, polyacrylonitrile, polyacetal, thermoplastic modified cellulose, polysulfone, thermoplastic polyester, PET, poly(ethyl acrylate), poly(methyl methacrylate), nylon, fluoropolymer, polyvinylidene fluoride, and ethylene tetrafluoroethylene.

11. The system of claim 1, wherein the flowable insulative material has a thermal conductivity of less than about 5 W/m-K.

12. An apparatus for thermally treating tissue, comprising:
  an elongate introducer having a proximal end, a distal end, and an interior passageway extending from the proximal end to an opening in the distal end;
  a flowable insulative material carried in or otherwise in fluid communication with the interior passageway;
  at least one electrode coupled to or proximate to the distal end of the introducer;
  an energy delivery actuator configured to controllably energize the at least one electrode; and
  a flow actuator configured to actuate a controlled flow of the flowable insulative material from the interior passageway through the distal end opening and outwardly from the distal end of the introducer;
  wherein the flowable insulative material comprises a thermochromic material.

13. A system for thermally treating tissue, comprising:
  an elongate introducer having a proximal end, a distal end, a first interior passageway extending from the proximal end to a first opening in the distal end, and a second interior passageway extending from the proximal end to a second opening in the distal end proximate the first opening,
  a flowable insulative material carried in or otherwise in fluid communication with the first interior passageway;
  a flowable conductive material carried in or otherwise in fluid communication with the second interior passageway;
  one or more actuation mechanisms configured to simultaneously actuate a controlled flow of the flowable insulative material out the first distal end opening, and a controlled flow of the flowable conductive material out the second distal end opening; and
  at least one electrode coupled to or proximate to the distal end of the introducer; and
  an energy delivery actuator configured to controllably energize the at least one electrode;
  wherein the flowable insulative material comprises a base polymer and dispersed nonconductive filler.

14. The system of claim 13, wherein the respective one or more actuation mechanisms and the first and second distal end openings are configured such that the respective flowable insulative material and flowable conductive material are simultaneously ejected out the respective first and second distal end openings and flow alongside one another outwardly from the distal end of the elongate introducer.

15. The system of claim 13, wherein the flowable insulative material has a thermal conductivity of less than about 5 W/m-K.

16. The system of claim 13, wherein the flowable insulative material comprises a thermochromic material.

* * * * *